US009975939B2

(12) United States Patent
Tolborg et al.

(10) Patent No.: US 9,975,939 B2
(45) Date of Patent: May 22, 2018

(54) GLUCAGON ANALOGUES

(71) Applicant: Zealand Pharma A/S, Glostrup (DK)

(72) Inventors: Jakob Lind Tolborg, Herlev (DK); Keld Fosgerau, Rødovre (DK); Pia Nørregaard, Lyngby (DK); Rasmus Just, Copenhagen N (DK); Ditte Riber, Broenshoej (DK); Dieter Wolfgang Hamprecht, Pozzolengo (IT); Robert Augustin, Ingelheim am Rhein (DE); Leo Thomas, Ingelheim am Rhein (DE); Wolfgang Rist, Ingelheim am Rhein (DE)

(73) Assignee: Zealand Pharma A/S, Glostrup (DK)

( * ) Notice: Subject to any disclaimer, the term of this patent is extended or adjusted under 35 U.S.C. 154(b) by 0 days. days.

(21) Appl. No.: 14/864,256

(22) Filed: Sep. 24, 2015

(65) Prior Publication Data

US 2016/0009777 A1    Jan. 14, 2016

Related U.S. Application Data

(63) Continuation of application No. 14/029,529, filed on Sep. 17, 2013, now Pat. No. 9,180,169.

(60) Provisional application No. 61/784,294, filed on Mar. 14, 2013, provisional application No. 61/701,952, filed on Sep. 17, 2012.

(30) Foreign Application Priority Data

Sep. 17, 2012   (EP) .................................... 12184744

(51) Int. Cl.
    A61K 38/00    (2006.01)
    C07K 14/605   (2006.01)
    A61K 38/26    (2006.01)
    A61K 45/06    (2006.01)

(52) U.S. Cl.
    CPC ............ *C07K 14/605* (2013.01); *A61K 38/26* (2013.01); *A61K 45/06* (2013.01)

(58) Field of Classification Search
    None
    See application file for complete search history.

(56) References Cited

U.S. PATENT DOCUMENTS

| 4,288,627 A | 9/1981 | Kubicek |
| 5,118,666 A | 6/1992 | Habener |
| 5,120,712 A | 6/1992 | Habener |
| 5,424,286 A | 6/1995 | Eng |
| 5,512,549 A | 4/1996 | Chen et al. |
| 5,523,449 A | 6/1996 | Prasad et al. |
| 5,545,618 A | 8/1996 | Buckley et al. |
| 5,614,492 A | 3/1997 | Habener |
| 5,631,224 A | 5/1997 | Efendic et al. |
| 5,670,360 A | 9/1997 | Thorens |
| 5,795,861 A | 8/1998 | Kolterman et al. |
| 5,846,747 A | 12/1998 | Thorens et al. |
| 5,846,937 A | 12/1998 | Drucker |
| 6,006,753 A | 12/1999 | Efendic |
| 6,051,689 A | 4/2000 | Thorens |
| 6,110,703 A | 8/2000 | Egel-Mitani et al. |
| 6,114,304 A | 9/2000 | Kolterman et al. |
| 6,136,784 A | 10/2000 | L'Italien et al. |
| 6,191,102 B1 | 2/2001 | DiMarchi et al. |
| 6,268,343 B1 | 7/2001 | Knudsen et al. |
| 6,271,241 B1 | 8/2001 | DeSimone et al. |
| 6,277,819 B1 | 8/2001 | Efendic |
| 6,284,725 B1 | 9/2001 | Coolidge et al. |
| 6,329,336 B1 | 12/2001 | Bridon et al. |
| 6,344,180 B1 | 2/2002 | Holst et al. |
| 6,358,924 B1 | 3/2002 | Hoffmann |
| 6,384,016 B1 | 5/2002 | Kaarsholm |
| 6,388,053 B1 | 5/2002 | Galloway et al. |
| 6,410,508 B1 | 6/2002 | Isales et al. |
| 6,410,511 B2 | 6/2002 | L'Italien et al. |
| 6,451,974 B1 | 9/2002 | Hansen |
| 6,458,924 B2 | 10/2002 | Knudsen et al. |
| 6,506,724 B1 | 1/2003 | Hiles et al. |
| 6,528,486 B1 | 3/2003 | Larsen et al. |
| 6,703,359 B1 | 3/2004 | Young et al. |
| 6,767,887 B1 | 7/2004 | Hoffmann et al. |
| 6,858,576 B1 | 2/2005 | Young et al. |
| 6,872,700 B1 | 3/2005 | Young et al. |
| 6,902,744 B1 | 6/2005 | Kolterman et al. |
| 6,924,264 B1 | 8/2005 | Prickett et al. |
| 6,956,026 B2 | 10/2005 | Beeley et al. |
| 6,989,366 B2 | 1/2006 | Beeley et al. |
| 7,056,734 B1 | 6/2006 | Egan et al. |
| 7,115,569 B2 | 10/2006 | Beeley et al. |

(Continued)

FOREIGN PATENT DOCUMENTS

| AU | 2008326324 | 5/2009 |
| CN | 101519446 | 9/2009 |

(Continued)

OTHER PUBLICATIONS

U.S. Appl. No. 61/784,294, Tolborg et al.
U.S. Appl. No. 14/843,047, Zealand Pharma A/S.
U.S. Appl. No. 60/132,018, Prickett et al.
Pan et al., "Design of a long acting peptide functioning as both a glucagon-like peptide-1 receptor agonist and a glucagon recegtor antagonist," J Biol Chem. 281 (18):12506-12515 (2006).
Action Closing Prosecution in Inter Partes Reexam 95/000,276, mailed Mar. 17, 2011 (25 pages).
Ally et al., "Rapid determination of creatine, phosphocreatine, purine bases and nucleotides (ATP, ADP, AMP, GTP, GDP) in heart biopsies by gradient ion-pair reversed-phase liquid chromatography," J Chromatogr. 575(1):19-27 (1992).

(Continued)

*Primary Examiner* — Thomas S Heard
(74) *Attorney, Agent, or Firm* — Clark & Elbing LLP

(57) ABSTRACT

The invention provides materials and methods for the treatment of obesity and excess weight, diabetes, and other associated metabolic disorders. In particular, the invention provides novel glucagon analog peptides effective in such methods. The peptides may mediate their effect by having increased selectivity for the GLP-1 receptor as compared to human glucagon.

4 Claims, No Drawings

(56) References Cited

U.S. PATENT DOCUMENTS

| | | |
|---|---|---|
| 7,138,375 B2 | 11/2006 | Beeley et al. |
| 7,153,825 B2 | 12/2006 | Young et al. |
| 7,157,555 B1 | 1/2007 | Beeley et al. |
| 7,220,721 B1 | 5/2007 | Beeley et al. |
| 7,223,725 B1 | 5/2007 | Beeley et al. |
| 7,226,990 B2 | 6/2007 | Knudsen et al. |
| 7,235,627 B2 | 6/2007 | Knudson et al. |
| 7,297,761 B2 | 11/2007 | Beeley et al. |
| 7,348,404 B2 | 3/2008 | Holm et al. |
| 7,399,489 B2 | 7/2008 | Kolterman et al. |
| 7,407,932 B2 | 8/2008 | Young et al. |
| 7,419,952 B2 | 9/2008 | Beeley et al. |
| 7,442,680 B2 | 10/2008 | Young et al. |
| 7,452,858 B2 | 11/2008 | Hiles et al. |
| 7,521,423 B2 | 4/2009 | Young et al. |
| 7,544,657 B2 | 6/2009 | Ebbehoj et al. |
| 7,601,691 B2 | 10/2009 | Bridon et al. |
| 7,608,692 B2 | 10/2009 | Prickett et al. |
| 7,623,530 B2 | 11/2009 | Hurtta |
| 7,683,030 B2 | 3/2010 | Prickett et al. |
| 7,691,963 B2 | 4/2010 | Prickett et al. |
| 7,696,161 B2 | 4/2010 | Beeley et al. |
| 7,700,549 B2 | 4/2010 | Beeley et al. |
| 7,741,269 B2 | 6/2010 | Young et al. |
| 7,858,740 B2 | 12/2010 | Beeley et al. |
| 7,928,065 B2 | 4/2011 | Young et al. |
| 7,935,786 B2 | 5/2011 | Larsen |
| 7,994,122 B2 | 8/2011 | Riber et al. |
| 8,026,210 B2 | 9/2011 | Young et al. |
| 8,057,822 B2 | 11/2011 | Prickett et al. |
| 8,097,698 B2 | 1/2012 | Knudsen et al. |
| 8,263,550 B2 | 9/2012 | Beeley et al. |
| 8,288,338 B2 | 10/2012 | Young et al. |
| 8,445,647 B2 | 5/2013 | Prickett et al. |
| 8,642,540 B2 | 2/2014 | Meier et al. |
| 8,642,541 B2 | 2/2014 | Meier et al. |
| 8,642,727 B2 | 2/2014 | Larsen et al. |
| 8,680,049 B2 | 3/2014 | Meier et al. |
| 8,685,919 B2 | 4/2014 | Meier et al. |
| 9,156,901 B2 | 10/2015 | Riber et al. |
| 9,169,310 B2 | 10/2015 | Riber et al. |
| 9,180,169 B2 | 11/2015 | Tolborg et al. |
| 9,403,894 B2 | 8/2016 | Meier et al. |
| 2002/0137666 A1 | 9/2002 | Beeley et al. |
| 2004/0106547 A1 | 6/2004 | Larsen et al. |
| 2005/0070469 A1 | 3/2005 | Bloom et al. |
| 2006/0057137 A1 | 3/2006 | Steiness |
| 2006/0194719 A1 | 8/2006 | Ebbehoj et al. |
| 2006/0293232 A1 | 12/2006 | Levy et al. |
| 2007/0111940 A1 | 5/2007 | Larsen et al. |
| 2009/0088369 A1 | 4/2009 | Steiness |
| 2010/0099601 A1 | 4/2010 | Weiss |
| 2010/0190701 A1 | 7/2010 | Day et al. |
| 2010/0240883 A1 | 9/2010 | Wu et al. |
| 2011/0144008 A1 | 6/2011 | Larsen et al. |
| 2011/0230397 A1 | 9/2011 | Carriero et al. |
| 2011/0245165 A1 | 10/2011 | Larsen et al. |
| 2011/0286981 A1 | 11/2011 | Meier et al. |
| 2011/0286982 A1 | 11/2011 | Meier et al. |
| 2011/0293586 A1 | 12/2011 | Meier et al. |
| 2011/0293587 A1 | 12/2011 | Meier et al. |
| 2011/0312878 A1 | 12/2011 | Larsen |
| 2012/0178670 A1 | 7/2012 | Riber et al. |
| 2013/0053304 A1 | 2/2013 | Wang et al. |
| 2013/0157929 A1 | 6/2013 | Riber et al. |
| 2013/0157935 A1 | 6/2013 | Meier et al. |
| 2013/0157953 A1 | 6/2013 | Petersen et al. |
| 2013/0316941 A1 | 11/2013 | Hamprecht et al. |
| 2014/0011733 A1 | 1/2014 | Fosgerau et al. |
| 2014/0080757 A1 | 3/2014 | Tolborg et al. |
| 2014/0127174 A1 | 5/2014 | Meier et al. |
| 2014/0127175 A1 | 5/2014 | Meier et al. |
| 2014/0187483 A1 | 7/2014 | Steiness |
| 2014/0336356 A1 | 11/2014 | Larsen et al. |
| 2015/0080295 A1 | 3/2015 | Meier et al. |
| 2015/0111817 A1 | 4/2015 | Riber et al. |
| 2015/0111826 A1 | 4/2015 | Riber et al. |
| 2015/0210744 A1 | 7/2015 | Riber et al. |
| 2015/0299281 A1 | 10/2015 | Just et al. |
| 2015/0322130 A1 | 11/2015 | DiMarchi et al. |
| 2015/0376257 A1 | 12/2015 | Riber et al. |
| 2016/0000883 A1 | 1/2016 | Fosgerau et al. |
| 2016/0120951 A1 | 5/2016 | Riber et al. |
| 2016/0304576 A1 | 10/2016 | Meier et al. |
| 2016/0347813 A1 | 12/2016 | Hamprecht et al. |

FOREIGN PATENT DOCUMENTS

| | | |
|---|---|---|
| CN | 101519446 A | 9/2009 |
| DE | 102008003566 | 7/2009 |
| DE | 102008003566 A1 | 7/2009 |
| DE | 102008003568 | 7/2009 |
| DE | 102008003568 A1 | 7/2009 |
| EP | 0082731 | 6/1983 |
| EP | 0082731 A1 | 6/1983 |
| EP | 1076066 A1 | 2/2001 |
| EP | 1196444 B1 | 6/2003 |
| EP | 1329458 A2 | 7/2003 |
| EP | 1421950 A1 | 5/2004 |
| EP | 2025684 | 2/2009 |
| EP | 2025684 A1 | 2/2009 |
| EP | 2028192 A1 | 2/2009 |
| EP | 1525219 B1 | 5/2009 |
| EP | 2112161 A2 | 10/2009 |
| JP | 2011-524418 A | 9/2011 |
| JP | 2012-511900 A | 5/2012 |
| WO | WO-91/11457 A1 | 8/1991 |
| WO | WO-91/17243 A1 | 11/1991 |
| WO | WO-93/18786 A1 | 9/1993 |
| WO | WO-95/05848 A1 | 3/1995 |
| WO | WO-97/46584 A1 | 12/1997 |
| WO | WO-98/05351 A1 | 2/1998 |
| WO | 98/08871 | 3/1998 |
| WO | 98/11125 | 3/1998 |
| WO | 98/11126 | 3/1998 |
| WO | WO-98/08531 A1 | 3/1998 |
| WO | WO-98/08871 A1 | 3/1998 |
| WO | WO-98/08873 A1 | 3/1998 |
| WO | WO-98/11125 A1 | 3/1998 |
| WO | WO-98/11126 A1 | 3/1998 |
| WO | WO-98/19698 A1 | 5/1998 |
| WO | WO-98/22577 A1 | 5/1998 |
| WO | WO-98/30231 A1 | 7/1998 |
| WO | WO-98/35033 A1 | 8/1998 |
| WO | WO-98/39022 A1 | 9/1998 |
| WO | WO-98/50351 A1 | 11/1998 |
| WO | WO-99/07404 A1 | 2/1999 |
| WO | 99/25727 | 5/1999 |
| WO | WO-99/25727 A2 | 5/1999 |
| WO | WO-99/25728 A1 | 5/1999 |
| WO | WO-99/40788 A1 | 8/1999 |
| WO | 99/46283 | 9/1999 |
| WO | WO-99/43707 A1 | 9/1999 |
| WO | WO-99/43708 A1 | 9/1999 |
| WO | WO-99/46283 A1 | 9/1999 |
| WO | WO-99/49788 A1 | 10/1999 |
| WO | WO-99/64060 A1 | 12/1999 |
| WO | WO-00/09666 A2 | 2/2000 |
| WO | 00/34331 | 6/2000 |
| WO | WO-00/34331 A2 | 6/2000 |
| WO | WO-00/41546 A2 | 7/2000 |
| WO | WO-00/41548 A2 | 7/2000 |
| WO | 00/55119 | 9/2000 |
| WO | 00/55184 | 9/2000 |
| WO | WO-00/55119 A1 | 9/2000 |
| WO | WO-00/55184 A1 | 9/2000 |
| WO | WO-00/66629 A1 | 11/2000 |
| WO | WO-00/73331 A2 | 12/2000 |
| WO | 01/04156 | 1/2001 |
| WO | WO-01/04156 A1 | 1/2001 |
| WO | WO-01/32158 A2 | 5/2001 |
| WO | WO-02/34285 A2 | 5/2002 |
| WO | 03/022304 | 3/2003 |
| WO | WO-03/022304 A1 | 3/2003 |

(56) References Cited

FOREIGN PATENT DOCUMENTS

| | | |
|---|---|---|
| WO | 03/053339 | 7/2003 |
| WO | 03/053460 | 7/2003 |
| WO | WO-03/053339 A2 | 7/2003 |
| WO | WO-03/053460 A1 | 7/2003 |
| WO | WO-2004/005342 A1 | 1/2004 |
| WO | 2004/062685 | 7/2004 |
| WO | WO-2004/062685 A2 | 7/2004 |
| WO | 2004/096854 | 11/2004 |
| WO | WO-2004/096854 A2 | 11/2004 |
| WO | WO-2005/072045 A2 | 8/2005 |
| WO | WO-2006/051110 A2 | 5/2006 |
| WO | WO-2006/097537 A2 | 9/2006 |
| WO | WO-2006/121860 A2 | 11/2006 |
| WO | 2006/134340 | 12/2006 |
| WO | WO-2006/134340 A2 | 12/2006 |
| WO | 2007/024899 | 3/2007 |
| WO | WO-2007/024899 A2 | 3/2007 |
| WO | 2007/056362 | 5/2007 |
| WO | WO-2007/056362 A2 | 5/2007 |
| WO | 2007/081824 | 7/2007 |
| WO | WO-2007/081824 A2 | 7/2007 |
| WO | WO-2007/095737 A1 | 8/2007 |
| WO | 2007/100535 | 9/2007 |
| WO | WO-2007/100535 A2 | 9/2007 |
| WO | 2008/010101 | 1/2008 |
| WO | WO-2008/010101 A2 | 1/2008 |
| WO | 2008/071972 | 6/2008 |
| WO | WO-2008/071010 A1 | 6/2008 |
| WO | WO-2008/071972 A1 | 6/2008 |
| WO | 2008/101017 | 8/2008 |
| WO | WO-2008/101017 A2 | 8/2008 |
| WO | 2008/152403 | 12/2008 |
| WO | WO-2008/152403 A1 | 12/2008 |
| WO | WO-2008/155257 A1 | 12/2008 |
| WO | 2009/067636 | 5/2009 |
| WO | WO-2009/067636 A2 | 5/2009 |
| WO | WO-2009/077737 A2 | 6/2009 |
| WO | 2009/087081 | 7/2009 |
| WO | 2009/087082 | 7/2009 |
| WO | WO-2009/087081 A2 | 7/2009 |
| WO | WO-2009/087082 A2 | 7/2009 |
| WO | 2009/129250 | 10/2009 |
| WO | 2009/132129 | 10/2009 |
| WO | WO-2009/129250 A2 | 10/2009 |
| WO | WO-2009/132129 A2 | 10/2009 |
| WO | 2009/152128 | 12/2009 |
| WO | 2009/155257 | 12/2009 |
| WO | 2009/155258 | 12/2009 |
| WO | WO-2009/152128 A1 | 12/2009 |
| WO | WO-2009/155257 A1 | 12/2009 |
| WO | WO-2009/155258 A2 | 12/2009 |
| WO | 2010/002283 | 1/2010 |
| WO | WO-2010/002283 A9 | 1/2010 |
| WO | WO-2010/011439 A2 | 1/2010 |
| WO | 201/014946 | 2/2010 |
| WO | WO-2010/014946 A2 | 2/2010 |
| WO | WO-2010/016940 A2 | 2/2010 |
| WO | WO-2010/029159 A1 | 3/2010 |
| WO | 2010/070251 | 6/2010 |
| WO | 2010/070252 | 6/2010 |
| WO | 2010/070253 | 6/2010 |
| WO | 2010/070255 | 6/2010 |
| WO | WO-2010/070251 A1 | 6/2010 |
| WO | WO-2010/070252 A1 | 6/2010 |
| WO | WO-2010/070253 A1 | 6/2010 |
| WO | WO-2010/070255 A1 | 6/2010 |
| WO | 2010/080606 | 7/2010 |
| WO | 2010/080609 | 7/2010 |
| WO | WO-2010/080606 A1 | 7/2010 |
| WO | WO-2010/080609 A1 | 7/2010 |
| WO | WO-2010/096052 A1 | 8/2010 |
| WO | WO-2010/148089 A1 | 12/2010 |
| WO | 2011/006497 | 1/2011 |
| WO | WO-2011/006497 A1 | 1/2011 |
| WO | 2011/088837 | 7/2011 |
| WO | WO-2011/080103 A1 | 7/2011 |
| WO | WO-2011/084808 A2 | 7/2011 |
| WO | WO-2011/088837 A1 | 7/2011 |
| WO | WO-2011/094337 A1 | 8/2011 |
| WO | WO-2011/117417 A1 | 9/2011 |
| WO | WO-2011/119657 A1 | 9/2011 |
| WO | WO-2011/134471 A1 | 11/2011 |
| WO | 2011/160630 | 12/2011 |
| WO | 2011/160633 | 12/2011 |
| WO | WO-2011/160630 A2 | 12/2011 |
| WO | WO-2011/160633 A1 | 12/2011 |
| WO | WO-2012/062803 A1 | 5/2012 |
| WO | WO-2012/062804 A1 | 5/2012 |
| WO | 2012/098462 | 7/2012 |
| WO | WO-2012/098462 A1 | 7/2012 |
| WO | WO-2012/130866 A1 | 10/2012 |
| WO | WO-2012/140117 A1 | 10/2012 |
| WO | WO-2012/150503 A2 | 11/2012 |
| WO | WO-2012/153196 A2 | 11/2012 |
| WO | WO-2012/167744 A1 | 12/2012 |
| WO | WO-2013/041678 A1 | 3/2013 |
| WO | 2013/092703 | 6/2013 |
| WO | WO-2013/092703 A2 | 6/2013 |
| WO | WO-2013/164483 A1 | 11/2013 |
| WO | WO-2014/016300 A1 | 1/2014 |
| WO | 2014/041195 | 3/2014 |
| WO | WO-2014/041195 A1 | 3/2014 |
| WO | WO-2015/067715 A2 | 5/2015 |
| WO | WO-2015/124612 A1 | 8/2015 |

OTHER PUBLICATIONS

Bailey et al., "Glucagon-like peptide-1 and the entero-insular axis in obese hyperglycaemic (ob/ob) mice," Life Sci. 40(6):521-525 (1987).

Ban et al., "Cardioprotective and vasodilatory actions of glucagon-like peptide 1 receptor are mediated through both glucagon-like peptide 1 receptor-dependent and -independent pathways," Circulation. 117(18):2340-2350 (2008).

Bedford et al., "Amino acid structure and 'difficult sequences' in solid phase peptide synthesis," Int J Peptide Protein Res. 40(3-4): 300-7 (1992).

Behme et al., "Glucagon-like peptide 1 improved glycemic control in Type 1 diabetes," BMC Endocr Disord. 3(1):1-9 (2003).

Burcelin et al., "Long-lasting antidiabetic effect of a dipeptidyl peptidase IV-resistant analog of glucagon-like peptide-1," Metabolism. 48(2):252-8 (1999).

Buse et al., "The effect of epinephrine, glucagon, and the nutritional state on the oxidation of branched chain amino acids and pyruvate by isolated hearts and diaphragms of the rat," J Biol Chem. 248(2):697-706 (1973).

Buse, "Progressive use of medical therapies in type 2 diabetes," Diabetes Spectrum. 13(4):211-20 (2000).

Byrne et al., "Inhibitory effects of hyperglycaemia on fed jejunal motility: potential role of hyperinsulinaemia," Eur J Clin Invest. 28(1):72-78 (1998).

Carpenter et al., "Rational design of stable lyophilized protein formulations: some practical advice," Pharm Res. 14(8):969-75 (1997).

Chen et al., "Evidence that the Diabetes gene encodes the leptin receptor: identification of a mutation in the leptin receptor gene in db/db mice," Cell. 84(3):491-5 (1996).

Chen et al., "Tissue-specific expression of unique mRNAs that encode proglucagon-derived peptides or exendin 4 in the lizard," J Biol Chem. 272(7):4108-4115 (1997).

Cleland et al., "The development of stable protein formulations: a close look at protein aggregation, deamidation, and oxidation," Crit Rev Ther Drug Carrier Syst. 10(4):307-77 (1993).

Coleman, "Effects of parabiosis of obese with diabetes and normal mice," Diabetologia. 9(4):294-8 (1973).

D'Alessio et al., "Glucagon-like peptide 1 enhances glucose tolerance both by stimulation of insulin release and by increasing insulin-independent glucose disposal," J Clin Invest 93(5):2263-2266 (1994).

(56) References Cited

OTHER PUBLICATIONS

De Boer et al., "The tac promoter: a functional hybrid derived from the trp and lac promoters," Proc Natl Acad Sci USA. 80(1):21-5 (1983).
Deacon et al., "Dipeptidyl peptidase IV inhibition potentiates the insulinotropic effect of glucagon-like peptide 1 in the anesthetized pig," Diabetes. 47(5):764-9 (1998).
Deacon et al., "Dipeptidyl peptidase IV resistant analogues of glucagon-like peptide-1 which have extended metabolic stability and improved biological activity," Diabetologia. 41(3):271-8 (1998).
Decision in Inter Partes Reexam for U.S. Appl. No. 95/000,276, filed Nov. 25, 2013 (29 pages).
Dickstein et al., "ESC Guidelines for the diagnosis and treatment of acute and chronic heart failure 2008: the Task Force for the diagnosis and treatment of acute and chronic heart failure 2008 of the European Society of Cardiology. Developed in collaboration with the Heart Failure Association of the ESC (HFA) and endorsed by the European Society of Intensive Care Medicine (ESICM)," Eur Heart J. 29(19):2388-442 (2008).
Drucker, "Glucagon-like peptides," Diabetes. 47(2):159-69 (1998).
Edvell et al., "Initiation of increased pancreatic islet growth in young normoglycemic mice (Umeå +/?)," Endocrinology. 140(2):778-83 (1999).
Ehrlich, "DNA cloning in Bacillus subtilis," Proc Natl Acad Sci USA. 75(3):1433-6 (1978).
EMEA Humalog Information: European Public Assessment Report (EPAR) and Scientific Discussions (11 pages) (2006).
European Medicines Agency, European Public Assessment Report (EPAR) for European Application 03762471.5, updated in Jan. 2006 (11 pages).
European Search Opinion and Extended European Search Report for European Patent Application No. 08016668.9, dated Jan. 27, 2009 (5 pages).
European Search Report for European Patent Application No. 09002937, dated Mar. 15, 2010 (5 pages).
European Search Report for European Patent Application No. 99610043, dated Jan. 18, 2000 (2 pages).
Extended European Search Report for European Patent Application No. 11774431.8, dated Sep. 30, 2013 (11 pages).
Farah et al., "Studies on the pharmacology of glucagon," J Pharmacol Exp Ther. 129:49-55 (1960).
Fineman et al., Abstract 343-OR: "AC2993 (Synthetic Exendin-4) added to existing metformin (Met) and/or Sulfonylurea (SFU) treatment improved glycemic control in patients with type 2 diabetes (DM2) during 28 days of treatment," Diabetes. 51(Supplement 2):A85, Abstract Book, 62nd Scientific Sessions (2002) (3 pages).
Göke et al., "Distribution of GLP-1 binding sites in the rat brain: Evidence that exendin-4 is a ligand of brain GLP-1 binding sites," Eur J Neurosci. 7(11):2294-2300 (1995).
Greig et al., "Once daily injection of exendin-4 to diabetic mice achieves long-term beneficial effects on blood glucose concentrations," Diabetologia. 42(1):45-50 (1999).
Grieve et al., "Emerging cardiovascular actions of the incretin hormone glucagon-like peptide-1: Potential therapeutic benefits beyond glycaemic control?," Br J Pharmacol. 157(8):1340-1351 (2009).
Gunn et al., "Central glucagon-like peptide-I in the control of feeding," Biochem Soc Trans. 24(2):581-4 (1996).
Guo et al., "3'-end-forming signals of yeast mRNA," Mol Cell Biol. 15(11):5983-5990 (1995).
Haffner et al., "Intensive lifestyle intervention or metformin on inflammation and coagulation in participants with impaired glucose tolerance," Diabetes. 54(5):1566-72 (2005).
Hamad et al., "Pharmacologic therapy of chronic heart failure," Am J Cardiovasc Drugs. 7(4):235-48 (2007).
Harikae, "The Effects of a Behavioral program in the obese NIDDM Patients-Observations on daily activity degree of obesity, and blood sugar control," Bulletin of the School of Nursing, Yamaguchi Prefectural University 2:1-12, 1998 (Abstract in English).
Heinrich et al., "Pre-proglucagon messenger ribonucleic acid: nucleotide and encoded amino acid sequences of the rat pancreatic complementary deoxyribonucleic acid," Endocrinology. 115(6):2176-2181 (1984).
Holst, "Enteroglucagon," Annu Rev Physiol. 59:257-271 (1997).
Holst, "Glucagon-like peptide-1, a gastrointestinal hormone with a pharmaceutical potential," Curr Med Chem. 6(11):1005-1017 (1999).
Holst, "The physiology of glucagon-like peptide 1," Physiol Rev. 87(4): 1409-39 (2007).
Hui et al, "The short half-life of glucagon-like peptide-1 in plasma does not reflect its long-lasting beneficial effects," Eur J Endocrinol. 146(6):863-9 (2002).
Ingwall et al., "Is the failing heart energy starved? On using chemical energy to support cardiac function," Circ Res. 95(2):135-45 (2004).
International Preliminary Examination Report for International Application No. PCT/DK03/00463, dated Sep. 20, 2004 (5 pages).
International Search Report and Written Opinion for International Application No. PCT/IB2012/001090, dated Jan. 25, 2013 (15 pages).
International Search Report and Written Opinion for International Patent Application No. PCT/EP2012/071766, dated Feb. 15, 2013 (10 pages).
International Search Report for International Application No. PCT/DK00/00393, dated Nov. 8, 2000 (3 pages).
International Search Report for International Application No. PCT/DK03/00463, dated Oct. 22, 2003 (7 pages).
International Search Report for International Application No. PCT/DK2011/050018, dated May 30, 2011 (4 pages).
International Search Report for International Application No. PCT/DK2011/050133 dated Oct. 6, 2011 (5 pages).
Jessup et al., "2009 focused update: ACCF/AHA Guidelines for the Diagnosis and Management of Heart Failure in Adults: a report of the American College of Cardiology Foundation/American Heart Association Task Force on Practice Guidelines: developed in collaboration with the International Society for Heart and Lung Transplantation," Circulation. 119:1977-2016 (2009).
Juntti-Berggren et al., "The antidiabetogenic effect of GLP-1 is maintained during a 7-day treatment period and improves diabetic dyslipoproteinemia in NIDDM patients," Diabetes Care. 19(11):1200-6 (1996).
Korc, "Islet growth factors: curing diabetes and preventing chronic pancreatitis?," J Clin Invest. 92(3):1113-4 (1993).
Krchnák et al., "Aggregation of resin-bound peptides using solid-phase peptide synthesis. Prediction of difficult sequences," Int J Peptide Protein Res. 42(5):450-4 (1993).
Larsen et al., "Sequence-assisted peptide synthesis (SAPS)," J Peptide Res. 52(6):470-6 (1998).
Leiter et al., "Influence of dietary carbohydrate on the induction of diabetes in C57BL/KsJ-db/db diabetes mice," J Nutr. 113(1):184-95 (1983).
Levey et al., "Activation of adenyl cyclase by glucagon in cat and human heart," Circ Res. 24(2):151-6 (1969).
Lopaschuk et al., "Measurements of fatty acid and carbohydrate metabolism in the isolated working rat heart," Mol Cell Biochem. 172(1-2):137-47 (1997).
López-Delgado et al., "Effects of glucagon-like peptide 1 on the kinetics of glycogen synthase a in hepatocytes from normal and diabetic rats," Endocrinology. 139(6):2811-2817 (1998).
Loyter et al., "Mechanisms of DNA uptake by mammalian cells: fate of exogenously added DNA monitored by the use of fluorescent dyes," Proc Natl Acad Sci USA. 79(2):422-6 (1982).
Manning et al., "Stability of protein pharmaceuticals," Pharm Res. 6(11):903-18 (1989).
Matthes et al., "Simultaneous rapid chemical synthesis of over one hundred oligonucleotides on a microscale," EMBO J. 3(4):801-805 (1984).
Mayer et al., "Effect of glucagon on cyclic 3',5'-AMP, phosphorylase activity and contractility of heart muscle of the rat," Circ Res. 26(2):225-233 (1970).

(56) References Cited

OTHER PUBLICATIONS

Meurer et al., "Properties of native and in vitro glycosylated forms of the glucagon-like peptide-1 receptor antagonist exendin (9-39)," Metabolism. 48(6):716-724 (1999).
Meyer et al., Effects of conformation on the Chemical Stability of Pharmaceutically Relevant Polypeptides. *Rational design of stable protein formulations*. Carpenter and Manning, 85-6 (2002).
Mojsov, "Structural requirements for biological activity of glucagon-like peptide-I," Int J Pept Protein Res. 40(3-4):333-343 (1992).
Nauck et al., "Glucagon-like peptide 1 and its potential in the treatment of non-insulin-dependent diabetes mellitus," Horm Metab Res. 29(9):411-416 (1997).
Navarro et al., "Colocalization of glucagon-like peptide-1 (GLP-1) receptors, glucose transporter GLUT-2, and glucokinase mRNAs in rat hypothalamic cells: evidence for a role of GLP-1 receptor agonists as an inhibitory signal for food and water intake," J Neurochem 67(5):1982-91 (1996).
Neubauer et al., "Myocardial phosphocreatine-to-ATP ratio is a predictor of mortality in patients with dilated cardiomyopathy," Circulation. 96(7):2190-2196 (1997) (9 pages).
Neumann et al., "Gene transfer into mouse lyoma cells by electroporation in high electric fields," EMBO J. 1(7):841-845 (1982).
Nikolaidis et al., "Active metabolite of GLP-1 mediates myocardial glucose uptake and improves left ventricular performance in conscious dogs with dilated cardiomyopathy," Am J Physiol Heart Circ Physiol. 289(6):H2401-H2408 (2005).
Nikolaidis et al., "Recombinant glucagon-like peptide-1 increases myocardial glucose uptake and improves left ventricular performance in conscious dogs with pacing-induced dilated cardiomyopathy," Circulation. 110(8):955-961 (2004).
Notice of Opposition for European Patent No. 1525219, dated Feb. 26, 2010 (24 pages).
Orskov, "Glucagon-like peptide-1, a new hormone of the entero-insular axis," Diabetologia. 35(8):701-711 (1992).
Owens et al., "Insulins today and beyond," The Lancet. 358:739-746 (2001).
Parkes et al., "Insulinotropic actions of exendin-4 and glucagon-like peptide-1 in vivo and in vitro," Metabolism. 50(5):583-9 (2001).
Partial European Search Report for European Patent Application No. 03005786, dated Oct. 23, 2003 (6 pages).
Partial European Search Report for European Patent Application No. 99610043, dated Jan. 18, 2000 (4 pages).
Pederson et al., "Improved glucose tolerance in Zucker Fatty Rats by oral administration of the dipeptidyl peptidase IV inhibitor isoleucine thiazolidide," Diabetes. 47(8):1253-1258 (1998).
Petersen et al., "ZP10—A new GLP-1 agonist that prevents diabetes progression and increases insulin mRNA expression in db/db mice," 38th Annual Meeting of the European Association for the Study of Diabetes (EASD). Budapest, Hungary, Sep. 1-5, 2002; Diabetologia. 45 (Suppl 1):A147, Abstract No. 447 (2002).
Pohl et al., "Molecular cloning of the helodermin and exendin-4 cDNAs in the lizard. Relationship to vasoactive intestinal polypeptide/pituitary adenylate cyclase activating polypeptide and glucagon-like peptide 1 and evidence against the existence of mammalian homologues," J Biol Chem. 273(16):9778-84 (1998).
Poon et al., "Exenatide improves glycemic control and reduces body weight in subjects with type 2 diabetes: a dose-ranging study," Diabetes Technol Ther. 7(3):467-77 (2005).
Pridal et al., "Absorption of glucagon-like peptide-1 can be protracted by zinc or protamine," Int J Pharm 136:53-59 (1996).
Raufman et al, "Truncated glucagon-like peptide-1 interacts with exendin receptors on dispersed acini from guinea pig pancreas. Identification of a mammalian analogue of the reptilian peptide exendin-4," J Biol Chem. 267(30):21432-7 (1992).
Raufman et al. "Exendin-3, a novel peptide from Heloderma horridum venom, interacts with vasoactive intestinal peptide receptors and a newly described receptor on dispersed acini from guinea pig pancreas. Description of exendin-3(9-39) amide, a specific exendin receptor antagonist," J Biol Chem. 266(5):2897-902 (1991).
Raufman, "Bioactive peptides from lizard venoms," Regul Pept. 61(1):1-18 (1996).
Ritzel et al., "A synthetic glucagon-like peptide-1 analog with improved plasma stability," J Endocrinol. 159(1):93-102 (1998).
Roach et al., "Improved postprandial glycemic control during treatment with humalog Mix25, a novel protamine-based insulin lispro formulation," Diabetes Care. 22(8):1258-61 (1999).
Robberecht et al., "Comparative efficacy of seven synthetic glucagon analogs, modified in position 1, 2, and/or 12, on liver and heart adenylate cyclase from rat," Peptides. 7(Suppl 1):109-112 (1986).
Rolin et al., "The long-acting GLP-1 derivative NN2211 ameliorates glycemia and increases beta-cell mass in diabetic mice," Am J Physiol Endocrinol Metab. 283(4):E745-52 (2002).
Rooman et al., "Gastrin stimulates beta-cell neogenesis and increases islet mass from transdifferentiated but not from normal exocrine pancreas tissue," Diabetes. 51(3):686-690 (2002).
Saraceni et al., "Effects of glucagon-like peptide-1 and long-acting analogues on cardiovascular and metabolic function," Drugs R D. 8(3):145-53 (2007).
Sowden et al., "Oxyntomodulin increases intrinsic heart rate in mice independent of the glucagon-like peptide-1 receptor," Am J Physiol Regul Integr Comp Physiol. 292(2): R962-70 (2007).
Stoffers et al., "Insulinotropic glucagon-like peptide 1 agonists stimulate expression of homeodomain protein IDX-1 and increases islet size in mouse pancreas," Diabetes. 49(5):741-8 (2000).
Suarez-Pinzon et al., "Combination therapy with epidermal growth factor and gastrin increases beta-cell mass and reverses hyperglycemia in diabetic NOD mice," Diabetes. 54(9):2596-601 (2005).
Suarez-Pinzon et al., "Combination therapy with glucagon-like peptide-1 and gastrin restores normoglycemia in diabetic NOD mice," Diabetes. 57(12):3281-8 (2008).
Tang-Christensen et al., "Central administration of GLP-1-(7-36) amide inhibits food and water intake in rats," Am J. Physiol. 271(4 Pt 2):R848-56 (1996).
Thorkildsen et al., "The exendin analogue ZP10 increases insulin mRNA expression in db/db mice," Nedergaard Symposium, Odense, Denmark, Jan. 24, 2002 (Poster presentation).
Thorkildsen et al., "ZP10—A New GLP-1 agonist that increases insulin mRNA expression," Nedergaard Symposium, Odense, Denmark, Jan. 24, 2002 (abstract only) (1 page).
Thorkildsen et al., "ZP10—A new GLP-1 agonist that prevents diabetes progression and increases insulin mRNA expression in db/db mice," 38th Annual Meeting of the European Associate for the Study of Diabetes (EASD), Budapest, Hungary, Sep. 1-5, 2002 (Poster presentation).
Tomita et al., "Pancreatic islets of obese hyperglycemic mice (ob/ob)," Pancreas. 7(3):367-375 (1992).
Tourrel et al., "Persistent improvement of type 2 diabetes in the Goto-Kakizaki Rat model by expansion of the beta-cell mass during the prediabetic period with glucagon-like peptide-1 or exendin-4," Diabetes. 51(5):1443-52 (2002).
Turton et al., "A role for glucagon-like peptide-1 in the central regulation of feeding," Nature 379(6560):69-72 (1996).
Uesaka et al., "Glucagon-like peptide isolated from the eel intestine: Effects on atrial beating," J Exp Bio. 204(Pt 17):3019-3026 (2001).
Underwood et al., "Crystal structure of glucagon-like peptide-1 in complex with the extracellular domain of the glucagon-like peptide-1 receptor," J Biol Chem. 285(1):723-30 (2010).
Uttenthal et al., "Molecular forms of glucagon-like peptide-1 in human pancreas and glucagonomas," J Clin Endocrinol Metab. 61(3):472-479 (1985).
Villa-Komaroff et al., "A bacterial clone synthesizing proinsulin," Proc Natl Acad Sci USA. 75(8):3727-3731 (1978).
Wang et al., "Glucagon-like peptide-1 treatment delays the onset of diabetes in 8 week-old db/db mice," Diabetologia. 45(9):1263-73 (2002).
Warnica, "Acute coronary syndromes (Heart Attack; Myocardial Infarction; Unstable Angina)," <http://www.merckmanuals.com/home/heart_and_blood_vessel_disorders/coronary_artery_disease/

(56) References Cited

OTHER PUBLICATIONS acute_coronary_syndromes_heart_attack_myocardial_infarction_unstable_angina.html?qt-congestive heart failure &alt=sh>, retrieved on Feb. 8, 2015 (8 pages).
Wettergren et al., "Truncated GLP-1 (proglucagon 78-107-amide) inhibits gastric and pancreatic functions in man," Dig Dis Sci. 38(4):665-73 (1993).
White, "A review of potential cardiovascular uses of intravenous glucagon administration," J Clin Pharmacol. 39(5):442-7 (1999).
Wiberg et al., "Replication and expression in mammalian cells of transfected DNA; description of an improved erythrocyte ghost fusion technique," Nucleic Acids Res. 11(21):7287-7302 (1983).
Xu et al., "Exendin-4 stimulates both beta-cell replication and neogenesis, resulting in increased beta-cell mass and improved glucose tolerance in diabetic rats," Diabetes. 48(12):2270-6 (1999).
Yabe et al., "Quantitative measurements of cardiac phosphorus metabolites in coronary artery disease by 31P magnetic resonance spectroscopy," Circulation. 92(1):15-23 (1995) (14 pages).
Young et al., "Glucose-lowering and insulin-sensitizing actions of exendin-4: studies in obese diabetic (ob/ob, db/db) mice, diabetic fatty zucker rats, and diabetic rhesus mondays (*Macaca mulatta*)," Diabetes. 48(5):1026-1034 (1999).
Young et al., "Physiological and genetic factors affecting transformation of Bacillus subtilis," J Bacteriol. 81:823-829 (1961).
Zander et al., "Additive glucose-lowering effects of glucagon-like peptide-1 and metformin in type 2 diabetes," Diabetes Care. 24(4):720-5 (2001).
Zhao et al., "Direct effects of glucagon-like peptide-1 on myocardial contractility and glucose uptake in normal and postischemic isolated rat hearts," J Pharmacol Exp Ther. 317(3):1106-1113 (2006).
Zhou et al., "Glucagon-like peptide-1 and exendin-4 convert pancreatic AR42J cells into glucagon- and insulin-producing cells," Diabetes. 48(12): 2358-2366 (1999).
Overgaard et al., "Inotropes and vasopressors: review of physiology and clinical use in cardiovascular disease," Circulation. 118(10):1047-56 (2008).
Fang et al., "Diabetic cardiomyopathy: evidence, mechanisms, and therapeutic implications, " Endocr Rev. 25(4):543-67 (2004).
Notice of Allowance and Allowed Claims for U.S. Appl. No. 13/383,783, dated Jun. 22, 2015 (5 pages).
Notice of Allowance, previously Allowed Claims and Amendment after Allowance for U.S. Appl. No. 13/704,299, dated Jun. 26, 2015 (15 pages).
Notice of Allowance, previously Allowed Claims and Amendment after Allowance for U.S. Appl. No. 14/029,529, dated Jun. 29, 2015 (14 pages).
Bell, "Heart failure: the frequent, forgotten, and often fatal complication of diabetes," Diabetes Care. 26(8):2433-41 (2003).
Lefèbvre, "The intriguing diversity of the glucagon gene products," Curr Diab Rep. 2(3):201-2 (2002).
Lvoff et al., "Glucagon in heart failure and in cardiogenic shock. Experience in 50 patients," Circulation. 45(3):534-42 (1972).
Diamant et al., "Diabetic cardiomyopathy in uncomplicated type 2 diabetes is associated with the metabolic syndrome and systemic inflammation," Diabetologia 48(8):1669-70 (2005).
Ebert et al., "Gastric inhibitory polypeptide," Clin Gastroenterol. 9(3):679-98 (1980).
Finan et al., "Reappraisal of GIP Pharmacology for Metabolic Diseases," Trends Mol Med. 22(5):359-76 (2016).
First Examination Report for New Zealand Patent Application No. 702333, dated Jun. 2, 2016 (4 pages).
Gault et al., "Administration of an acylated GLP-1 and GIP preparation provides added beneficial glucose-lowering and insulinotropic actions over single incretins in mice with Type 2 diabetes and obesity," Clin Sci (Lond). 121(3):107-17 (2011).
Green et al., "Structurally modified analogues of glucagon-like peptide-1 (GLP-1) and glucose-dependent insulinotropic polypeptide (GIP) as future antidiabetic agents," Curr Pharm Des. 10(29):3651-62 (2004).

Hansson, "Inflammation, atherosclerosis, and coronary artery disease," N Engl J Med. 352(16):1685-95 (2005).
International Search Report and Written Opinion for PCT/EP2013/059319, dated Sep. 12, 2013 (12 pages).
International Search Report and Written Opinion for PCT/EP2013/065519, dated Dec. 6, 2013 (11 pages).
Irwin et al., "Antidiabetic potential of two novel fatty acid derivatised, N-terminally modified analogues of glucose-dependent insulinotropic polypeptide (GIP): N-AcGIP(LysPAL16) and N-AcGIP(LysPAL37)," Biol Chem. 386(7):679-87 (2005).
Irwin et al., "GIP(Lys16PAL) and GIP(Lys37PAL): novel long-acting acylated analogues of glucose-dependent insulinotropic polypeptide with improved antidiabetic potential," J Med Chem. 49(3):1047-54 (2006).
Malde et al., "Understanding interactions of gastric inhibitory polypeptide (GIP) with its G-protein coupled receptor through NMR and molecular modeling," J Pept Sci. 13(5):287-300 (2007).
Manhart et al., "Structure-function analysis of a series of novel GIP analogues containing different helical length linkers," Biochemistry. 42(10):3081-8 (2003).
Matsumoto et al., "Plasma Incretin Levels and Dipeptidyl Peptidase-4 Activity in Patients with Obstructive Sleep Apnea," Ann Am Thorac Soc. 13(8):1378-87 (2016).
Runge et al., "Differential structural properties of GLP-1 and exendin-4 determine their relative affinity for the GLP-1 receptor N-terminal extracellular domain," Biochemistry. 46(19):5830-40 (2007).
Chabenne et al., "Optimization of the native glucagon sequence for medicinal purposes," J Diabetes Sci Technol. 4(6):1322-31 (2010).
Office Action for Colombian Application No. 16089238, dated Sep. 13, 2017 (18 pages).
Periasamy et al., "Molecular basis of diastolic dysfunction," Heart Fail Clin. 4(1):13-21 (2008).
Yasgur, "Premature ventricle contractions in heart failure: a closer examination," http://www.thecardiologyadvisor.com/heart-failure/premature-ventricle-contractions-in-heart-failure/article/515445/, retrieved Sep. 10, 2017 (3 pages).
Abbrecht et al., "Erythrocyte life-span in mice acclimatized to different degrees of hypoxia," J Appl Physiol. 32(4):443-445 (1972).
Adelhorst et al., "Structure-activity studies of glucagon-like peptide-1," J Biol Chem 269(9):6275-6278 (1994).
Altschul et al., "Local alignment statistics," Methods Enzymol. 266:460-480 (1996).
Authier et al., "Endosomal proteolysis of glucagon at neutral pH generates the bioactive degradation product miniglucagon-(19-29)," Endocrinology. 144(12):5353-5364 (2003).
Blache et al., "Endopeptidase from rat liver membranes, which generates miniglucagon from glucagon," J Biol Chem. 268(29):21748-21753 (1993).
Cavanaugh et al., "Isolation and structural characterization of proglucagon-derived peptides, pancreatic polypeptide, and somatostatin from the urodele Amphiuma tridactylum," Gen Comp Endocrinol. 101(1):12-20 (1996).
Chan et al., "Suppression of weight gain by glucagon in obese Zucker rats," Exp Mol Path. 40(3):320-327 (1984).
Cohen et al., "Oxyntomodulin suppresses appetite and reduces food intake in humans," J Clin Endocrinol Metab. 88(10):4696-4701 (2003).
Dakin et al., "Oxyntomodulin inhibits food intake in the rat," Endocrinology. 142(10):4244-4250 (2001).
Dakin et al., "Peripheral oxyntomodulin reduces food intake and body weight gain in rats," Endocrinology. 145(6):2687-2695 (2004).
Day et al., "A new glucagon and GLP-1 co-agonist eliminates obesity in rodents," Nat Chem Biol. 5(10):749-757 (2009).
Delgado et al., "The uses and properties of PEG-linked proteins," Crit Rev Ther Drug Carrier Syst. 9(3,4):249-304 (1992).
Druce et al., "Investigation of structure-activity relationships of Oxyntomodulin (Oxm) using Oxm analogs," Endocrinology. 150(4):1712-1721 (2009).

(56) References Cited

OTHER PUBLICATIONS

England et al., "Glucagon carboxyl-terminal derivatives: Preparation, purification and characterization," Biochemistry. 21(5):940-950 (1982).
Francis et al., "PEGylation of cytokines and other therapeutic proteins and peptides: the importance of biological optimisation of coupling techniques," Int J Hematol. 68(1):1-18 (1998).
Frandsen et al., "Glucagon: structure-function relationships investigated by sequence deletions," Hoppe Seylers Z Physiol Chem. 362(6):665-677 (1981).
Gelfanov et al., Discovery and structural optimization of high affinity co-agonists at the glucagon and GLP-1 receptors. Understanding Biology Using Peptides. Sylvie E. Blondelle, 763-764 (2005).
Göke et al., "Exendin-4 is a high potency agonist and truncated exendin-(9-39)-amide an antagonist at the glucagon-like peptide 1-(7-36)-amide receptor of insulin-secreting beta-cells," J Biol Chem. 268(26):19650-19655 (1993).
Gombotz et al. "Biodegradable polymers for protein and peptide drug delivery," Bioconjug Chem. 6(4):332-351 (1995).
Hjorth et al., "Glucagon and glucagon-like peptide 1: Selective receptor recognition via distinct peptide epitopes," J Biol Chem. 269(48):30121-30124 (1994).
Hruby et al., "The design and biological activities of glucagon agonists and antagonists, and their use in examining the mechanisms of glucose action," Curr Med Chem—Imm, Endoc Metab Agents. 1(3):199-215 (2001).
Hudecz et al., "Synthesis, conformation, biodistribution, and in vitro cytotoxicity of daunomycin-branched polypeptide conjugates," Bioconjug Chem. 3(1):49-57 (1992).
International Search Report for International Application No. PCT/DK2010/000099, dated Dec. 2, 2010 (2 pages).
Joshi et al., "The estimation of glutaminyl deamidation and aspartyl cleavage rates in glucagon," Int J Pharm. 273(1-2):213-219 (2004).
Kallenbach et al., Role of the peptide bond in protein structure and folding. The Amide Linkage: Selected Structural Aspects in Chemistry, Biochemistry, and Materials Science. Greenberg, Breneman, Liebman, 599-625 (2000).
Knudsen et al., "Potent derivatives of glucagon-like peptide-1 with pharmacokinetic properties suitable for once daily administration," J Med Chem. 43(9):1664-1669 (2000).
Madsen et al., "Structure-activity and protraction relationship of long-acting glucagon-like peptide-1 derivatives: importance of fatty acid length, polarity, and bulkiness," J Med Chem. 50(54):6126-6132 (2007).
McKee et al., "Receptor binding and adenylate cyclase activities of glucagon analogues modified in the N-terminal region," Biochemistry. 25(7):1650-1656 (1986).
NCBI Blast for Accession No. 721913A, retrieved on Dec. 15, 2009 (1 page).
Pan et al., "Design of a long acting peptide functioning as both a glucagon-like peptide-1 receptor agonist and a glucagon receptor antagonist," J Biol Chem. 281(18):12506-12515 (2006).
Parlevliet et al., "Oxyntomodulin ameliorates glucose intolerance in mice fed a high-fat diet," Am J Physiol Endocrinol Metab. 294(1):E142-E147 (2008).
Pratesi et al., "Poly-L-aspartic acid as a carrier for doxorubicin: a comparative in vivo study of free and polymer-bound drug," Br J Cancer. 52(6):841-848 (1985).
Tsukada et al., "An anti-alpha-fetoprotein antibody-daunorubicin conjugate with a novel poly-L-glutamic acid derivative as intermediate drug carrier," J Natl Cancer Inst. 73(3):721-729 (1984).
Unson et al., "Glucagon antagonists: contribution to binding and activity of the amino-terminal sequence 1-5, position 12, and the putative alpha-helical segment 19-27," J Biol Chem. 264(2):789-794 (1989).
Unson et al., "Identification of an essential serine residue in glucagon: implication for an active site triad," Proc Natl Acad Sci USA. 91(2):454-458 (1994).
Unson et al., "Positively charged residues at positions 12, 17, and 18 of glucagon ensure maximum biological potency," J Biol Chem. 273(17):10308-10312 (1998).
Zalipsky, "Functionalized poly(ethylene glycol) for preparation of biologically relevant conjugates," Bioconjug Chem. 6(2):150-165 (1995).
Zhu et al., "The role of dipeptidyl peptidase IV in the cleavage of glucagon family peptides: in vivo metabolism of pituitary adenylate cyclase activating polypeptide-(1-38)," J Biol Chem. 278(25):22418-22423 (2003).
International Search Report for International Application No. PCT/DK2011/000067, dated Dec. 9, 2011 (4 pages).
Jaya et al., "Mechanism of hypocholesterolemic action of glucagon," J Biosci. 12(2):111-4 (1987).
Hostrup et al., Modification of Peptides and Proteins. Delivery Technologies for Biopharmaceuticals: Peptides, Proteins, Nucleic Acids and Vaccines. Jorgensen, Nielsen, 171-91 (2009).
Parlevliet et al., "CNTO736, a novel glucagon-like peptide-1 receptor agonist, ameliorates insulin resistance and inhibits very low-density lipoprotein production in high-fat-fed mice." J Pharmacol Exp Ther. 328(1):240-8 (2009).
Written Opinion for Singapore Application No. 201209089-0, dated Nov. 8, 2013 (10 pages).
Communication from the European Patent Office for European Patent Application No. 08875673.9, dated Jul. 4, 2012 (6 pages).
Written Opinion of the International Searching Authority for PCT/GB2008/002041, dated Sep. 9, 2008 (6 pages).
International Search Report for PCT/GB2008/002041, dated Sep. 9, 2008 (3 pages).
International Search Report for PCT/GB2008/004157, dated Jun. 4, 2009 (21 pages).
International Search Report and Written Opinion for PCT/GB2008/004121, dated Jun. 30, 2009 (25 pages).
International Search Report and Written Opinion for PCT/GB2008/004130, dated Mar. 25, 2009 (17 pages).
International Search Report and Written Opinion for PCT/GB2008/004132, dated Jun. 10, 2009 (16 pages).
International Search Report for PCT/DK2011/000072, dated Dec. 6, 2011 (3 pages).
International Search Report for International Application No. PCT/IB2012/000134, dated Jun. 25, 2012 (3 pages).
Wermuth et al., "Glossary of terms used in medicinal chemistry," Pure & Appl Chem. 70(5):1129-43 (1998).
European Search Report from European Patent Application No. 07016032.0, completed Jan. 28, 2008 (8 pages).
International Preliminary Report on Patentability for PCT/GB2008/002041, dated Dec. 17, 2009 (7 pages).
Protest of U.S. Appl. No. 12/664,534 Pursuant 37 CFR 1.291, dated Jan. 13, 2010 (14 pages).
Pocai, "Glucagon signaling in the heart: activation or inhibition?," Mol Metab. 4(2):81-2 (2015).
Goldstein et al., "Effects of chronic heart failure on the capacity of glucagon to enhance contractility and adenyl cyclase activity of human papillary muscles," Circulation. 44(4):638-648 (1971).
Arnold, "Heart failure," <http://www.merckmanuals.com/home/heart_and_blood_vessel_disorders/heart_failure/heart_failure.html?qt=congestive heart failure&alt=sh>, retrieved on Feb. 8, 2015 (12 pages).
Mehta, "Diabetic cardiomyopathy: insights into pathogenesis, diagnostic challenges, and therapeutic options," Intl J Pharm Sci Res. 3(10):3565-3576 (2012).
Ali et al., "Cardiomyocyte glucagon receptor signaling modulates outcomes in mice with experimental myocardial infarction," Mol Metab. 4(2):132-143 (2015).
Eng et al., "Isolation and characterization of exendin-4, an exendin-3 analogue, from Heloderma suspectum venom. Further evidence for an exendin receptor on dispersed acini from guinea pig pancreas.," J Biol Chem. 267(11):7402-7405 (1992).
Pocai et al., "Glucagon-like peptide 1/glucagon receptor dual agonism reverses obesity in mice," Diabetes. 58(10):2258-66 (2009).

(56) References Cited

OTHER PUBLICATIONS

Rose et al., "Insulin proteinase liberates from glucagon a fragment known to have enhanced activity against Ca2+ + Mg2+-dependent ATPase," Biochem J. 256(3):847-51 (1988).
International Preliminary Report on Patentability for PCT/EP2013/069286, completed Jan. 19, 2015 (40 pages).
International Search Report and Written Opinion for PCT/EP2013/069286, dated Dec. 18, 2013 (16 pages).
Written Opinion for PCT/DK2011/000072, dated Dec. 6, 2011 (6 pages).

SEQUENCE LISTING

<160> NUMBER OF SEQ ID NOS: 46

<210> SEQ ID NO 1
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 1

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Leu Ser

```
            20                  25

<210> SEQ ID NO 2
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 2

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Ser Ala
            20                  25

<210> SEQ ID NO 3
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 3

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Arg Ala
            20                  25

<210> SEQ ID NO 4
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 4

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Leu Ser Ala
            20                  25

<210> SEQ ID NO 5
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
```

```
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 5

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Glu Ser Ala
            20                  25

<210> SEQ ID NO 6
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 6

His Ser Gln Gly Thr Phe Thr Ser Asp Tyr Ser Arg Tyr Leu Asp Ser
1               5                   10                  15

Xaa Ala Ala Glu Asp Phe Val Glu Trp Leu Leu Arg Ala
            20                  25

<210> SEQ ID NO 7
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 7

His Ser Gln Gly Thr Phe Thr Ser Asp Tyr Ser Lys Tyr Leu Asp Ser
1               5                   10                  15

Xaa Ala Ala Glu Asp Phe Val Glu Trp Leu Leu Arg Ala
            20                  25

<210> SEQ ID NO 8
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 8

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Ser
            20                  25
```

```
<210> SEQ ID NO 9
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 9

His Ser Gln Gly Thr Phe Thr Ser Asp Tyr Ser Lys Tyr Leu Asp Ser
1               5                   10                  15

Xaa Ala Ala His Asp Phe Val Glu Trp Leu Leu Arg
            20                  25

<210> SEQ ID NO 10
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 10

His Ser Gln Gly Thr Phe Thr Ser Asp Tyr Ser Lys Tyr Leu Asp Glu
1               5                   10                  15

Xaa Ala Ala His Glu Phe Val Glu Trp Leu Glu Ser Ala
            20                  25

<210> SEQ ID NO 11
<211> LENGTH: 28
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 11

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Leu Ser
            20                  25

<210> SEQ ID NO 12
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)
```

-continued

```
<400> SEQUENCE: 12

His Ser Gln Gly Thr Phe Thr Ser Asp Tyr Ser Arg Tyr Leu Asp Ser
1               5                   10                  15

Xaa Ala Ala His Asp Phe Val Glu Trp Leu Leu Ser Ala
            20                  25

<210> SEQ ID NO 13
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 13

His Xaa Gln Gly Thr Phe Thr Ser Asp Tyr Ser Lys Tyr Leu Asp Ser
1               5                   10                  15

Xaa Ala Ala His Asp Phe Val Glu Trp Leu Leu Ser Ala
            20                  25

<210> SEQ ID NO 14
<211> LENGTH: 29
<212> TYPE: PRT
<213> ORGANISM: Artificial Sequence
<220> FEATURE:
<223> OTHER INFORMATION: Synthetic construct: Peptide X of Claim 2
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 14

His Xaa Gln Gly Thr Phe Thr Ser Asp Tyr Ser Lys Tyr Leu Asp Glu
1               5                   10                  15

Xaa Arg Ala Lys Asp Phe Ile Glu Trp Leu Leu Ser Ala
            20                  25

<210> SEQ ID NO 15
<211> LENGTH: 29
<212> TYPE: PRT
<213> ORGANISM: Artificial Sequence
<220> FEATURE:
<223> OTHER INFORMATION: Synthetic construct: Peptide X of Claim 3
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 15

His Xaa Gln Gly Thr Phe Thr Ser Asp Tyr Ser Lys Tyr Leu Asp Glu
1               5                   10                  15
```

```
Xaa Ala Ala Lys Asp Phe Ile Glu Trp Leu Glu Ser Ala
            20                  25

<210> SEQ ID NO 16
<211> LENGTH: 29
<212> TYPE: PRT
<213> ORGANISM: Artificial Sequence
<220> FEATURE:
<223> OTHER INFORMATION: Synthetic construct: Peptide X of Claim 6
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 16

His Xaa Gln Gly Thr Phe Thr Ser Asp Tyr Ser Lys Tyr Leu Asp Ser
1               5                   10                  15

Xaa Ala Ala Glu Asp Phe Val Glu Trp Leu Glu Ser Ala
            20                  25

<210> SEQ ID NO 17
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 17

His Xaa His Gly Thr Phe Thr Ser Asp Tyr Ser Lys Tyr Leu Glu Ser
1               5                   10                  15

Xaa Ala Ala Glu Glu Phe Ile Glu Trp Leu Glu Ser Ala
            20                  25

<210> SEQ ID NO 18
<211> LENGTH: 29
<212> TYPE: PRT
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 18

His Ser His Gly Thr Phe Thr Ser Asp Tyr Ser Lys Tyr Leu Glu Glu
1               5                   10                  15

Xaa Ala Ala His Glu Phe Ile Glu Trp Leu Ser Ala
            20                  25

<210> SEQ ID NO 19
<211> LENGTH: 29
<212> TYPE: PRT
```

```
<213> ORGANISM: Artificial Sequence
<220> FEATURE:
<223> OTHER INFORMATION: Synthetic construct: Peptide X of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 19

His Xaa His Gly Thr Phe Thr Ser Asp Tyr Ser Lys Tyr Leu Glu Glu
1               5                   10                  15

Xaa Ala Ala His Glu Phe Val Glu Trp Leu Glu Ser Ala
            20                  25

<210> SEQ ID NO 20
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 20

His Xaa Gln Gly Thr Phe Thr Ser Asp Tyr Ser Lys Tyr Leu Glu Glu
1               5                   10                  15

Xaa Ala Ala Lys Asp Phe Ile Glu Trp Leu Glu Ser Ala
            20                  25

<210> SEQ ID NO 21
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 21

His Xaa Gln Gly Thr Phe Thr Ser Asp Tyr Ser Lys Tyr Leu Glu Ser
1               5                   10                  15

Xaa Ala Ala Glu Asp Phe Ile Glu Trp Leu Glu Ser Ala
            20                  25

<210> SEQ ID NO 22
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
```

```
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 22

His Ser Gln Gly Thr Phe Thr Ser Asp Tyr Ser Lys Tyr Leu Glu Glu
1               5                   10                  15

Xaa Ala Ala Lys Asp Phe Ile Glu Trp Leu Glu Ser Ala
            20                  25

<210> SEQ ID NO 23
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 23

His Xaa Gln Gly Thr Phe Thr Ser Asp Tyr Ser Lys Tyr Leu Glu Ser
1               5                   10                  15

Xaa Ala Ala His Asp Phe Val Glu Trp Leu Glu Ser Ala
            20                  25

<210> SEQ ID NO 24
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Aib
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)

<400> SEQUENCE: 24

His Xaa Gln Gly Thr Phe Thr Ser Asp Tyr Ser Lys Tyr Leu Glu Ser
1               5                   10                  15

Xaa Ala Ala Glu Asp Phe Val Glu Trp Leu Glu Ser Ala
            20                  25

<210> SEQ ID NO 25
<211> LENGTH: 29
<212> TYPE: PRT
<213> ORGANISM: Artificial Sequence
<220> FEATURE:
<223> OTHER INFORMATION: Synthetic construct: Peptide X of Claim 8
<220> FEATURE:
<221> NAME/KEY: MOD_RES
<222> LOCATION: (2)..(2)
<223> OTHER INFORMATION: Xaa is D-Ser
<220> FEATURE:
<221> NAME/KEY: MOD_RES
<222> LOCATION: (17)..(17)
<223> OTHER INFORMATION: Lys, optionally containing a lipophilic or
      polymeric substitute or Lys(Hexadecanoyl-isoGlu)
```

```
<400> SEQUENCE: 25

His Xaa Gln Gly Thr Phe Thr Ser Asp Tyr Ser Lys Tyr Leu Asp Glu
1               5                   10                  15

Xaa Ala Ala Lys Asp Phe Ile Glu Trp Leu Glu Ser Ala
            20                  25

<210> SEQ ID NO 26
<211> LENGTH: 29
<212> TYPE: PRT
<213> ORGANISM: Homo sapiens

<400> SEQUENCE: 26

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr
            20                  25

<210> SEQ ID NO 27
<211> LENGTH: 8
<212> TYPE: PRT
<213> ORGANISM: Homo sapiens

<400> SEQUENCE: 27

Lys Arg Asn Arg Asn Asn Ile Ala
1               5

<210> SEQ ID NO 28
<211> LENGTH: 37
<212> TYPE: PRT
<213> ORGANISM: Homo sapiens

<400> SEQUENCE: 28

His Ser Gln Gly Thr Phe Thr Ser Asp Tyr Ser Lys Tyr Leu Asp Ser
1               5                   10                  15

Arg Arg Ala Gln Asp Phe Val Gln Trp Leu Met Asn Thr Lys Arg Asn
            20                  25                  30

Arg Asn Asn Ile Ala
        35

<210> SEQ ID NO 29
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (29)..(48)
<223> OTHER INFORMATION: May be present or absent. If present,
      represents   a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 29

His Xaa Gln Gly Thr Phe Thr Ser Asp Tyr Ser Lys Tyr Leu Asp Ser
1               5                   10                  15

Lys Ala Ala His Asp Phe Val Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
```

<210> SEQ ID NO 30
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 30

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 31
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 31

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 32
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr, Cys, Glu, Lys, Arg, Dbu, Dpr and Orn

<400> SEQUENCE: 32

His Xaa Gln Gly Thr Phe Thr Ser Asp Tyr Ser Lys Tyr Leu Asp Ser
1               5                   10                  15

Lys Ala Ala His Asp Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 33
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 33

His Ser Gln Gly Thr Phe Thr Ser Asp Tyr Ser Arg Tyr Leu Asp Ser
1               5                   10                  15

Lys Ala Ala Glu Asp Phe Val Glu Trp Leu Leu Arg Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 34
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 34

His Ser Gln Gly Thr Phe Thr Ser Asp Tyr Ser Lys Tyr Leu Asp Ser
1               5                   10                  15

Lys Ala Ala Glu Asp Phe Val Glu Trp Leu Leu Arg Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 35
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:

-continued

```
<221> NAME/KEY: VARIANT
<222> LOCATION: (29)..(48)
<223> OTHER INFORMATION: May be present or absent. If present,
      represents  a sequence of 1-20 amino acid units
      independently
      selected from the group consisting of Ala, Leu, Ser, Thr, Tyr,
      Cys, Glu, Lys, Arg, Dbu, Dpr and Orn

<400> SEQUENCE: 35

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 36
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (29)..(48)
<223> OTHER INFORMATION: May be present or absent. If present,
      represents  a sequence of 1-20 amino acid units
      independently
      selected from the group consisting of Ala, Leu, Ser, Thr, Tyr,
      Cys, Glu, Lys, Arg, Dbu, Dpr and Orn

<400> SEQUENCE: 36

His Ser Gln Gly Thr Phe Thr Ser Asp Tyr Ser Lys Tyr Leu Asp Ser
1               5                   10                  15

Lys Ala Ala His Asp Phe Val Glu Trp Leu Leu Arg Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

<210> SEQ ID NO 37
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents  a sequence of 1-20 amino acid units
      independently
      selected from the group consisting of Ala, Leu, Ser, Thr, Tyr,
      Cys, Glu, Lys, Arg, Dbu, Dpr and Orn

<400> SEQUENCE: 37

His Ser Gln Gly Thr Phe Thr Ser Asp Tyr Ser Lys Tyr Leu Asp Glu
1               5                   10                  15

Lys Ala Ala His Glu Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 38
<211> LENGTH: 48
<212> TYPE: PRT
<213> ORGANISM: Artificial Sequence
<220> FEATURE:
<223> OTHER INFORMATION: Synthetic construct: Peptide X-Z of Claim 1
```

```
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (29)..(48)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 38

His Xaa Gln Gly Thr Phe Thr Ser Asp Tyr Ser Lys Tyr Leu Asp Glu
1               5                   10                  15

Lys Arg Ala Lys Asp Phe Ile Glu Trp Leu Leu Ser Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
            35                  40                  45

<210> SEQ ID NO 39
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 39

His Ser Gln Gly Thr Phe Thr Ser Asp Tyr Ser Arg Tyr Leu Asp Ser
1               5                   10                  15

Lys Ala Ala His Asp Phe Val Glu Trp Leu Leu Ser Ala Xaa Xaa Xaa
            20                  25                  30

Xaa Xaa Xaa Xaa Xaa Xaa Xaa Xaa Xaa Xaa Xaa Xaa Xaa Xaa Xaa
            35                  40                  45

Xaa

<210> SEQ ID NO 40
<211> LENGTH: 49
<212> TYPE: PRT
<213> ORGANISM: Artificial Sequence
<220> FEATURE:
<223> OTHER INFORMATION: Synthetic construct: Peptide X-Z of Claim 3
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 40

His Xaa Gln Gly Thr Phe Thr Ser Asp Tyr Ser Lys Tyr Leu Asp Glu
1               5                   10                  15

Lys Ala Ala Lys Asp Phe Ile Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
```

```
                35                  40                  45
Xaa

<210> SEQ ID NO 41
<211> LENGTH: 49
<212> TYPE: PRT
<213> ORGANISM: Artificial Sequence
<220> FEATURE:
<223> OTHER INFORMATION: Synthetic construct: Peptide X-Z of Claim 6
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 41

His Xaa Gln Gly Thr Phe Thr Ser Asp Tyr Ser Lys Tyr Leu Asp Ser
1               5                   10                  15

Lys Ala Ala Glu Asp Phe Val Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 42
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present,
      represents  a sequence of 1-20 amino acid units independently
      selected from the group consisting of Ala, Leu, Ser, Thr, Tyr,
      Cys, Glu, Lys, Arg, Dbu, Dpr and Orn

<400> SEQUENCE: 42

His Xaa His Gly Thr Phe Thr Ser Asp Tyr Ser Lys Tyr Leu Glu Ser
1               5                   10                  15

Lys Ala Ala Glu Glu Phe Ile Glu Trp Leu Glu Ser Ala Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Xaa

<210> SEQ ID NO 43
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: VARIANT
<222> LOCATION: (30)..(49)
<223> OTHER INFORMATION: May be present or absent. If present,
```

-continued represents a sequence of 1-20 amino acid units independently selected from the group consisting of Ala, Leu, Ser, Thr, Tyr, Cys, Glu, Lys, Arg, Dbu, Dpr and Orn

<400> SEQUENCE: 43

```
His Ser His Gly Thr Phe Thr Ser Asp Tyr Ser Lys Tyr Leu Glu Glu
 1               5                  10                  15

Lys Ala Ala His Glu Phe Ile Glu Trp Leu Glu Ser Ala Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa
```

<210> SEQ ID NO 44
<211> LENGTH: 49
<212> TYPE: PRT
<213> ORGANISM: Artificial Sequence
<220> FEATURE:
<223> OTHER INFORMATION: Synthetic construct: Peptide X-Z of Claim 1
<220> FEATURE:
<221> NAME/KEY: MOD_RES
<222> LOCATION: (2)..(2)
<223> OTHER INFORMATION: Aib
<220> FEATURE:
<221> NAME/KEY: VARIANT
<222> LOCATION: (30)..(49)
<223> OTHER INFORMATION: May be present or absent. If present, represents a sequence of 1-20 amino acid units independently selected from the group consisting of Ala, Leu, Ser, Thr, Tyr, Cys, Glu, Lys, Arg, Dbu, Dpr and Orn

<400> SEQUENCE: 44

```
His Xaa His Gly Thr Phe Thr Ser Asp Tyr Ser Lys Tyr Leu Glu Glu
 1               5                  10                  15

Lys Ala Ala His Glu Phe Val Glu Trp Leu Glu Ser Ala Xaa Xaa Xaa
                20                  25                  30

Xaa Xaa Xaa Xaa Xaa Xaa Xaa Xaa Xaa Xaa Xaa Xaa Xaa Xaa Xaa
            35                  40                  45

Xaa
```

<210> SEQ ID NO 45
<211> LENGTH: 477
<212> TYPE: PRT
<213> ORGANISM: Homo sapiens

<400> SEQUENCE: 45

```
Met Pro Pro Cys Gln Pro Gln Arg Pro Leu Leu Leu Leu Leu Leu Leu
 1               5                  10                  15

Leu Ala Cys Gln Pro Gln Val Pro Ser Ala Gln Val Met Asp Phe Leu
                20                  25                  30

Phe Glu Lys Trp Lys Leu Tyr Gly Asp Gln Cys His His Asn Leu Ser
                35                  40                  45

Leu Leu Pro Pro Pro Thr Glu Leu Val Cys Asn Arg Thr Phe Asp Lys
         50                  55                  60

Tyr Ser Cys Trp Pro Asp Thr Pro Ala Asn Thr Thr Ala Asn Ile Ser
 65                  70                  75                  80

Cys Pro Trp Tyr Leu Pro Trp His His Lys Val Gln His Arg Phe Val
                85                  90                  95

Phe Lys Arg Cys Gly Pro Asp Gly Gln Trp Val Arg Gly Pro Arg Gly
                100                 105                 110

Gln Pro Trp Arg Asp Ala Ser Gln Cys Gln Met Asp Gly Glu Glu Ile
```

```
            115                 120                 125
Glu Val Gln Lys Glu Val Ala Lys Met Tyr Ser Ser Phe Gln Val Met
130                 135                 140

Tyr Thr Val Gly Tyr Ser Leu Ser Leu Gly Ala Leu Leu Ala Leu
145                 150                 155                 160

Ala Ile Leu Gly Gly Leu Ser Lys Leu His Cys Thr Arg Asn Ala Ile
                165                 170                 175

His Ala Asn Leu Phe Ala Ser Phe Val Leu Lys Ala Ser Ser Val Leu
            180                 185                 190

Val Ile Asp Gly Leu Leu Arg Thr Arg Tyr Ser Gln Lys Ile Gly Asp
        195                 200                 205

Asp Leu Ser Val Ser Thr Trp Leu Ser Asp Gly Ala Val Ala Gly Cys
    210                 215                 220

Arg Val Ala Ala Val Phe Met Gln Tyr Gly Ile Val Ala Asn Tyr Cys
225                 230                 235                 240

Trp Leu Leu Val Glu Gly Leu Tyr Leu His Asn Leu Leu Gly Leu Ala
                245                 250                 255

Thr Leu Pro Glu Arg Ser Phe Phe Ser Leu Tyr Leu Gly Ile Gly Trp
            260                 265                 270

Gly Ala Pro Met Leu Phe Val Val Pro Trp Ala Val Val Lys Cys Leu
        275                 280                 285

Phe Glu Asn Val Gln Cys Trp Thr Ser Asn Asp Asn Met Gly Phe Trp
    290                 295                 300

Trp Ile Leu Arg Phe Pro Val Phe Leu Ala Ile Leu Ile Asn Phe Phe
305                 310                 315                 320

Ile Phe Val Arg Ile Val Gln Leu Leu Val Ala Lys Leu Arg Ala Arg
                325                 330                 335

Gln Met His His Thr Asp Tyr Lys Phe Arg Leu Ala Lys Ser Thr Leu
            340                 345                 350

Thr Leu Ile Pro Leu Leu Gly Val His Glu Val Val Phe Ala Phe Val
        355                 360                 365

Thr Asp Glu His Ala Gln Gly Thr Leu Arg Ser Ala Lys Leu Phe Phe
370                 375                 380

Asp Leu Phe Leu Ser Ser Phe Gln Gly Leu Leu Val Ala Val Leu Tyr
385                 390                 395                 400

Cys Phe Leu Asn Lys Glu Val Gln Ser Glu Leu Arg Arg Arg Trp His
                405                 410                 415

Arg Trp Arg Leu Gly Lys Val Leu Trp Glu Glu Arg Asn Thr Ser Asn
            420                 425                 430

His Arg Ala Ser Ser Ser Pro Gly His Gly Pro Pro Ser Lys Glu Leu
        435                 440                 445

Gln Phe Gly Arg Gly Gly Gly Ser Gln Asp Ser Ser Ala Glu Thr Pro
    450                 455                 460

Leu Ala Gly Gly Leu Pro Arg Leu Ala Glu Ser Pro Phe
465                 470                 475

<210> SEQ ID NO 46
<211> LENGTH: 463
<212> TYPE: PRT
<213> ORGANISM: Homo sapiens

<400> SEQUENCE: 46

Met Ala Gly Ala Pro Gly Pro Leu Arg Leu Ala Leu Leu Leu Leu Gly
1               5                   10                  15
```

```
Met Val Gly Arg Ala Gly Pro Arg Pro Gln Gly Ala Thr Val Ser Leu
             20              25              30

Trp Glu Thr Val Gln Lys Trp Arg Glu Tyr Arg Arg Gln Cys Gln Arg
         35              40              45

Ser Leu Thr Glu Asp Pro Pro Ala Thr Asp Leu Phe Cys Asn Arg
     50              55              60

Thr Phe Asp Glu Tyr Ala Cys Trp Pro Asp Gly Glu Pro Gly Ser Phe
65              70              75              80

Val Asn Val Ser Cys Pro Trp Tyr Leu Pro Trp Ala Ser Ser Val Pro
                 85              90              95

Gln Gly His Val Tyr Arg Phe Cys Thr Ala Glu Gly Leu Trp Leu Gln
             100             105             110

Lys Asp Asn Ser Ser Leu Pro Trp Arg Asp Leu Ser Glu Cys Glu Glu
         115             120             125

Ser Lys Arg Gly Glu Arg Ser Ser Pro Glu Glu Gln Leu Leu Phe Leu
     130             135             140

Tyr Ile Ile Tyr Thr Val Gly Tyr Ala Leu Ser Phe Ser Ala Leu Val
145             150             155             160

Ile Ala Ser Ala Ile Leu Leu Gly Phe Arg His Leu His Cys Thr Arg
                 165             170             175

Asn Tyr Ile His Leu Asn Leu Phe Ala Ser Phe Ile Leu Arg Ala Leu
             180             185             190

Ser Val Phe Ile Lys Asp Ala Ala Leu Lys Trp Met Tyr Ser Thr Ala
         195             200             205

Ala Gln Gln His Gln Trp Asp Gly Leu Leu Ser Tyr Gln Asp Ser Leu
     210             215             220

Ser Cys Arg Leu Val Phe Leu Leu Met Gln Tyr Cys Val Ala Ala Asn
225             230             235             240

Tyr Tyr Trp Leu Leu Val Glu Gly Val Tyr Leu Tyr Thr Leu Leu Ala
                 245             250             255

Phe Ser Val Leu Ser Glu Gln Trp Ile Phe Arg Leu Tyr Val Ser Ile
             260             265             270

Gly Trp Gly Val Pro Leu Leu Phe Val Val Pro Trp Gly Ile Val Lys
         275             280             285

Tyr Leu Tyr Glu Asp Glu Gly Cys Trp Thr Arg Asn Ser Asn Met Asn
     290             295             300

Tyr Trp Leu Ile Ile Arg Leu Pro Ile Leu Phe Ala Ile Gly Val Asn
305             310             315             320

Phe Leu Ile Phe Val Arg Val Ile Cys Ile Val Val Ser Lys Leu Lys
                 325             330             335

Ala Asn Leu Met Cys Lys Thr Asp Ile Lys Cys Arg Leu Ala Lys Ser
             340             345             350

Thr Leu Thr Leu Ile Pro Leu Leu Gly Thr His Glu Val Ile Phe Ala
         355             360             365

Phe Val Met Asp Glu His Ala Arg Gly Thr Leu Arg Phe Ile Lys Leu
     370             375             380

Phe Thr Glu Leu Ser Phe Thr Ser Phe Gln Gly Leu Met Val Ala Ile
385             390             395             400

Leu Tyr Cys Phe Val Asn Asn Glu Val Gln Leu Glu Phe Arg Lys Ser
                 405             410             415

Trp Glu Arg Trp Arg Leu Glu His Leu His Ile Gln Arg Asp Ser Ser
             420             425             430

Met Lys Pro Leu Lys Cys Pro Thr Ser Ser Leu Ser Ser Gly Ala Thr
```

```
            435                 440                 445
Ala Gly Ser Ser Met Tyr Thr Ala Thr Cys Gln Ala Ser Cys Ser
   450                 455                 460
```

GLUCAGON ANALOGUES

CROSS-REFERENCE TO RELATED APPLICATIONS

This application claims the benefit of U.S. Provisional Application No. 61/701,952, filed on Sep. 17, 2012, European Application No. 12184744.6, filed on Sep. 17, 2012, and U.S. Provisional Application No. 61/784,294, filed on Mar. 14, 2013, which are hereby incorporated by reference.

FIELD OF THE INVENTION

The present invention relates to glucagon analogues and their medical use, for example in the treatment of obesity and excess weight, diabetes, and other metabolic disorders.

BACKGROUND OF THE INVENTION

Pre-proglucagon is a 158 amino acid precursor polypeptide that is differentially processed in the tissues to form a number of structurally related proglucagon-derived peptides, including glucagon (Glu), glucagon-like peptide-1 (GLP-1), glucagon-like peptide-2 (GLP-2), and oxyntomodulin (OXM). These molecules are involved in a wide variety of physiological functions, including glucose homeostasis, insulin secretion, gastric emptying and intestinal growth, as well as regulation of food intake.

Glucagon is a 29-amino acid peptide that corresponds to amino acids 53 to 81 of pre-proglucagon. Oxyntomodulin (OXM) is a 37 amino acid peptide which includes the complete 29 amino acid sequence of glucagon with an octapeptide carboxyterminal extension (amino acids 82 to 89 of pre-proglucagon, and termed "intervening peptide 1" or IP-1. The major biologically active fragment of GLP-1 is produced as a 30-amino acid, C-terminally amidated peptide that corresponds to amino acids 98 to 127 of pre-proglucagon.

Glucagon helps maintain the level of glucose in the blood by binding to glucagon receptors on hepatocytes, causing the liver to release glucose—stored in the form of glycogen—through glycogenolysis. As these stores become depleted, glucagon stimulates the liver to synthesize additional glucose by gluconeogenesis. This glucose is released into the bloodstream, preventing the development of hypoglycemia.

GLP-1 decreases elevated blood glucose levels by improving glucose-stimulated insulin secretion and promotes weight loss chiefly through decreasing food intake.

OXM is released into the blood in response to food ingestion and in proportion to meal calorie content. OXM has been shown to suppress appetite and inhibit food intake in humans (Cohen et al, Journal of Endocrinology and Metabolism, 88, 4696-4701, 2003; WO 2003/022304). In addition to those anorectic effects, which are similar to those of GLP-1, OXM must also affect body weight by another mechanism, since rats treated with oxyntomodulin show less body weight gain than pair-fed rats (Bloom, Endocrinology 2004, 145, 2687). Treatment of obese rodents with OXM also improves their glucose tolerance (Parlevliet et al, Am J Physiol Endocrinol Metab, 294, E142-7, 2008) and suppresses body weight gain (WO 2003/022304).

OXM activates both the glucagon and the GLP-1 receptors with a two-fold higher potency for the glucagon receptor over the GLP-1 receptor, but is less potent than native glucagon and GLP-1 on their respective receptors. Human glucagon is also capable of activating both receptors, though with a strong preference for the glucagon receptor over the GLP-1 receptor. GLP-1 on the other hand is not capable of activating glucagon receptors. The mechanism of action of oxyntomodulin is not well understood. In particular, it is not known whether some of the extrahepatic effects of the hormone are mediated through the GLP-1 and glucagon receptors, or through one or more unidentified receptors.

Other peptides have been shown to bind and activate both the glucagon and the GLP-1 receptor (Hjort et al, Journal of Biological Chemistry, 269, 30121-30124, 1994) and to suppress body weight gain and reduce food intake (see, for example, WO 2006/134340, WO 2007/100535, WO 2008/10101, WO 2008/152403, WO 2009/155257, WO 2009/155258, WO2010/070252, WO2010/070253, WO2010/070255, WO2010/070251, WO2011/006497, WO2011/160630, WO2011/160633).

Obesity is a globally increasing health problem is associated with various diseases, particularly cardiovascular disease (CVD), type 2 diabetes, obstructive sleep apnea, certain types of cancer, and osteoarthritis. As a result, obesity has been found to reduce life expectancy. According to 2005 projections by the World Health Organization there are 400 million adults (age >15) classified as obese worldwide. In the US, obesity is now believed to be the second-leading cause of preventable death after smoking.

The rise in obesity drives an increase in diabetes, and approximately 90% of people with type 2 diabetes may be classified as obese. There are 246 million people worldwide with diabetes, and by 2025 it is estimated that 380 million will have diabetes. Many have additional cardiovascular risk factors, including high/aberrant LDL and triglycerides and low HDL.

SUMMARY OF THE INVENTION

In a first aspect, the invention provides a compound having the formula:

$$R^1—X—Z—R^2$$

wherein $R^1$ is H, $C_{1-4}$ alkyl, acetyl, formyl, benzoyl or trifluoroacetyl;

$R^2$ is OH or $NH_2$;

X is a peptide which has the formula:

```
                                        (SEQ ID NO: 1)
      H-Aib-QGTFTSDYSKYLDSKAAHDFVEWLLS (SEQ ID NO: 2)
      HSQGTFTSDYSKYLDSKAAHDFVEWLLSA (SEQ ID NO: 4)
      H-Aib-QGTFTSDYSKYLDEKAAKDFIEWLLSA (SEQ ID NO: 5)
      H-Aib-QGTFTSDYSKYLDSKAAHDFVEWLESA (SEQ ID NO: 6)
      HSQGTFTSDYSRYLDSKAAEDFVEWLLRA (SEQ ID NO: 7)
      HSQGTFTSDYSKYLDSKAAEDFVEWLLRA (SEQ ID NO: 8)
      HSQGTFTSDYSKYLDSKAAHDFVEWLLS (SEQ ID NO: 9)
      HSQGTFTSDYSKYLDSKAAHDFVEWLLR (SEQ ID NO: 10)
      HSQGTFTSDYSKYLDEKAAHEFVEWLESA
```

-continued

```
                                          (SEQ ID NO: 11)
H-Aib-QGTFTSDYSKYLDEKRAKDFIEWLLS (SEQ ID NO: 12)
HSQGTFTSDYSRYLDSKAAHDFVEWLLSA (SEQ ID NO: 17)
H-Aib-HGTFTSDYSKYLESKAAEEFIEWLESA (SEQ ID NO: 18)
HSHGTFTSDYSKYLEEKAAHEFIEWLESA (SEQ ID NO: 19)
H-Aib-HGTFTSDYSKYLEEKAAHEFVEWLESA
``` and Z is absent or is a sequence of 1-20 amino acid units independently selected from the group consisting of Ala, Leu, Ser, Thr, Tyr, Cys, Glu, Lys, Arg, Dbu, Dpr and Orn; or a pharmaceutically acceptable salt or solvate thereof.

In a second aspect, the invention provides a compound of the formula:

$R^1$—X—OH wherein
$R^1$ is H, $C_{1-4}$ alkyl, acetyl, formyl, benzoyl or trifluoroacetyl;
and X is a peptide of SEQ ID NO: 3, 13 or 14:

```
                                          (SEQ ID NO: 3)
HSQGTFTSDYSKYLDSKAAHDFVEWLLRA (SEQ ID NO: 13)
H-Aib-QGTFTSDYSKYLDSKAAHDFVEWLLSA (SEQ ID NO: 14)
H-Aib-QGTFTSDYSKYLDEKRAKDFIEWLLSA
``` or a pharmaceutically acceptable salt or solvate thereof.

In a third aspect, the invention provides a compound having the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 15:

```
                                          (SEQ ID NO: 15)
H-Aib-QGTFTSDYSKYLDEKAAKDFIEWLESA
``` or which differs from SEQ ID NO: 15 at up to three of the following positions whereby, if different from SEQ ID NO: 15:
   the residue at position 2 is selected from Ser and D-Ser
   the residue at position 3 is selected from His and Hse
   the residue at position 12 is Arg
   the residue at position 15 is Glu
   the residue at position 16 is Ser
   the residue at position 18 is Arg
   the residue at position 20 is selected from His and Glu
   the residue at position 21 is Glu
   the residue at position 23 is Val
   the residue at position 28 is selected from Arg and Glu
   the residue at position 29 is absent;
   and Z is absent or is a sequence of 1-20 amino acid units independently selected from the group consisting of Ala, Leu, Ser, Thr, Tyr, Cys, Glu, Lys, Arg, Dbu, Dpr and Orn; or a pharmaceutically acceptable salt or solvate thereof.

In certain embodiments, the residue at position 20 is not variable and is His.

The compound may have the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 15:

```
                                          (SEQ ID NO: 15)
H-Aib-QGTFTSDYSKYLDEKAAKDFIEWLESA
``` or which differs from SEQ ID NO: 15 at one or both of the following positions whereby, if different from SEQ ID NO: 15:
   the residue at position 21 is Glu
   the residue at position 23 is Val
   and Z is absent or is a sequence of 1-20 amino acid units independently selected from the group consisting of Ala, Leu, Ser, Thr, Tyr, Cys, Glu, Lys, Arg, Dbu, Dpr and Orn; or a pharmaceutically acceptable salt or solvate thereof.

In a fourth aspect, the invention provides a compound having the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 16:

```
                                          (SEQ ID NO: 16)
H-Aib-QGTFTSDYSKYLDSKAAEDFVEWLESA
``` or which differs from SEQ ID NO: 16 at up to three of the following positions whereby, if different from SEQ ID NO: 16:
   the residue at position 2 is selected from Ser and D-Ser
   the residue at position 3 is selected from His and Hse
   the residue at position 12 is Arg
   the residue at position 15 is Glu
   the residue at position 16 is Glu
   the residue at position 18 is Arg
   the residue at position 20 is selected from Lys and His
   the residue at position 21 is Glu
   the residue at position 23 is Ile
   the residue at position 28 is selected from Arg and Glu
   the residue at position 29 is absent
   and Z is absent or is a sequence of 1-20 amino acid units independently selected from the group consisting of Ala, Leu, Ser, Thr, Tyr, Cys, Glu, Lys, Arg, Dbu, Dpr and Orn; or a pharmaceutically acceptable salt or solvate thereof.

The compound may have the formula:

$R^1$—X—Z—$R^2$ wherein
$R^1$ is H, $C_{1-4}$ alkyl, acetyl, formyl, benzoyl or trifluoroacetyl;
$R^2$ is OH or $NH_2$;
X is a peptide of SEQ ID NO: 16:

```
                                          (SEQ ID NO: 16)
H-Aib-QGTFTSDYSKYLDSKAAEDFVEWLESA
``` or which differs from SEQ ID NO: 16 at one or both of the following positions whereby, if different from SEQ ID NO: 16:

the residue at position 21 is Glu
the residue at position 23 is Ile
and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt or solvate thereof.

A compound of the third or fourth aspects of the invention may comprise a peptide X having the sequence:

```
                                        (SEQ ID NO: 15)
H-Aib-QGTFTSDYSKYLDEKAAKDFIEWLESA (SEQ ID NO: 16)
H-Aib-QGTFTSDYSKYLDSKAAEDFVEWLESA (SEQ ID NO: 20)
H-Aib-QGTFTSDYSKYLEEKAAKDFIEWLESA (SEQ ID NO: 21)
H-Aib-QGTFTSDYSKYLESKAAEDFIEWLESA (SEQ ID NO: 22)
HSQGTFTSDYSKYLEEKAAKDFIEWLESA (SEQ ID NO: 23)
H-Aib-QGTFTSDYSKYLESKAAHDFVEWLESA (SEQ ID NO: 24)
H-Aib-QGTFTSDYSKYLESKAAEDFVEWLESA
or (SEQ ID NO: 25)
H-DSer-QGTFTSDYSKYLDEKAAKDFIEWLESA.
```

An any aspect, the compound of the invention may have the formula:

```
H-H-Aib-QGTFTSDYSKYLDSKAAHDFVEWLLS-OH

H-HSQGTFTSDYSKYLDSKAAHDFVEWLLSA-OH

H-H-Aib-QGTFTSDYSKYLDEKAAKDFIEWLLSA-NH2

H-H-Aib-QGTFTSDYSKYLDSKAAHDFVEWLESA-NH2

H-HSQGTFTSDYSRYLDSKAAEDFVEWLLRA-NH2

H-HSQGTFTSDYSKYLDSKAAEDFVEWLLRA-NH2

H-HSQGTFTSDYSKYLDSKAAHDFVEWLLS-NH2

H-HSQGTFTSDYSKYLDSKAAHDFVEWLLR-OH

H-HSQGTFTSDYSKYLDEKAAHEFVEWLESA-NH2

H-H-Aib-QGTFTSDYSKYLDEKRAKDFIEWLLS-OH

H-HSQGTFTSDYSRYLDSKAAHDFVEWLLSA-NH2

H-HSQGTFTSDYSKYLDSKAAHDFVEWLLRA-OH

H-H-Aib-QGTFTSDYSKYLDSKAAHDFVEWLLSA-OH

H-H-Aib-QGTFTSDYSKYLDEKRAKDFIEWLLSA-OH

H-H-Aib-QGTFTSDYSKYLDEKAAKDFIEWLESA-NH2

H-H-Aib-QGTFTSDYSKYLDSKAAEDFVEWLESA-NH2

H-Aib-HGTFTSDYSKYLESKAAEEFIEWLESA-OH

H-HSHGTFTSDYSKYLEEKAAHEFIEWLESA-OH

H-H-Aib-HGTFTSDYSKYLEEKAAHEFVEWLESA-NH2

H-H-Aib-QGTFTSDYSKYLEEKAAKDFIEWLESA-NH2

H-H-Aib-QGTFTSDYSKYLESKAAEDFIEWLESA-NH2

H-HSQGTFTSDYSKYLEEKAAKDFIEWLESA-NH2

H-H-Aib-QGTFTSDYSKYLESKAAHDFVEWLESA-NH2

H-H-Aib-QGTFTSDYSKYLESKAAEDFVEWLESA-NH2

H-H-DSer-QGTFTSDYSKYLDEKAAKDFIEWLESA-NH2
``` or may be a pharmaceutically acceptable salt or solvate thereof.

For the avoidance of doubt, in compounds of the third and fourth aspects of the invention, those positions which are not expressly stated to permit variability are intended to be fixed and thus only include the stated residue at those positions.

In all aspects of the invention, one or more of the amino acid side chains in the peptide X or Z (where present) may be conjugated to a lipophilic substituent.

Preferably, one or more of the amino acid side chains in the peptide X is conjugated to the lipophilic substituent.

A lipophilic substituent may have the formula $Z^1$ wherein $Z^1$ is a lipophilic moiety conjugated (covalently linked) directly to the side chain of the relevant residue of X or Z, or $Z^1Z^2$ where $Z^1$ is a lipophilic moiety, $Z^2$ is a spacer, and $Z^1$ is conjugated to the side chain of the residue of X or Z via $Z^2$.

Additionally or alternatively, one or more of the amino acid side chains in peptide X or Z (where present) is conjugated to a polymeric substituent.

In certain embodiments, the peptide X or X—Z carries only one lipophilic substituent and/or only one polymeric substituent.

Lipophilic and polymeric substituents are described in more detail below.

The lipophilic moiety and/or polymeric substituent may be conjugated to the side chain of any suitable residue. A lysine residue may be particularly suitable, e.g. a lysine residue at position 12 (if present) or 17.

Thus peptide X may have the formula:

```
H-Aib-QGTFTSDYSKYLDSK*AAHDFVEWLLS

HSQGTFTSDYSKYLDSK*AAHDFVEWLLSA

H-Aib-QGTFTSDYSKYLDEK*AAKDFIEWLLSA

H-Aib-QGTFTSDYSKYLDSK*AAHDFVEWLESA

HSQGTFTSDYSRYLDSK*AAEDFVEWLLRA

HSQGTFTSDYSKYLDSK*AAEDFVEWLLRA

HSQGTFTSDYSKYLDSK*AAHDFVEWLLS

HSQGTFTSDYSKYLDSK*AAHDFVEWLLR

HSQGTFTSDYSKYLDEK*AAHEFVEWLESA

H-Aib-QGTFTSDYSKYLDEK*RAKDFIEWLLS

HSQGTFTSDYSRYLDSK*AAHDFVEWLLSA

HSQGTFTSDYSKYLDSK*AAHDFVEWLLRA

H-Aib-QGTFTSDYSKYLDSK*AAHDFVEWLLSA

H-Aib-QGTFTSDYSKYLDEK*RAKDFIEWLLSA
```

-continued

```
H-Aib-QGTFTSDYSKYLDEK*AAKDFIEWLESA

H-Aib-QGTFTSDYSKYLDSK*AAEDFVEWLESA

H-Aib-HGTFTSDYSKYLESK*AAEEFIEWLESA

HSHGTFTSDYSKYLEEK*AAHEFIEWLESA

H-Aib-HGTFTSDYSKYLEEK*AAHEFVEWLESA

H-Aib-QGTFTSDYSKYLEEK*AAKDFIEWLESA

H-Aib-QGTFTSDYSKYLESK*AAEDFIEWLESA

HSQGTFTSDYSKYLEEK*AAKDFIEWLESA

H-Aib-QGTFTSDYSKYLESK*AAHDFVEWLESA

H-Aib-QGTFTSDYSKYLESK*AAEDFVEWLESA

H-DSer-QGTFTSDYSKYLDEK*AAKDFIEWLESA
``` where "*" indicates the position of a lipohilic or polymeric substituent, particularly a lipophilic substituent.

The compound of the invention may have the formula:

```
H-H-Aib-QGTFTSDYSKYLDSK*AAHDFVEWLLS-OH

H-HSQGTFTSDYSKYLDSK*AAHDFVEWLLSA-OH

H-H-Aib-QGTFTSDYSKYLDEK*AAKDFIEWLLSA-NH₂

H-H-Aib-QGTFTSDYSKYLDSK*AAHDFVEWLESA-NH₂

H-HSQGTFTSDYSRYLDSK*AAEDFVEWLLRA-NH₂

H-HSQGTFTSDYSKYLDSK*AAEDFVEWLLRA-NH₂

H-HSQGTFTSDYSKYLDSK*AAHDFVEWLLS-NH₂

H-HSQGTFTSDYSKYLDSK*AAHDFVEWLLR-OH

H-HSQGTFTSDYSKYLDEK*AAHEFVEWLESA-NH₂

H-H-Aib-QGTFTSDYSKYLDEK*RAKDFIEWLLS-OH

H-HSQGTFTSDYSRYLDSK*AAHDFVEWLLSA-NH₂

H-HSQGTFTSDYSKYLDSK*AAHDFVEWLLRA-OH

H-H-Aib-QGTFTSDYSKYLDSK*AAHDFVEWLLSA-OH

H-H-Aib-QGTFTSDYSKYLDEK*RAKDFIEWLLSA-OH

H-H-Aib-QGTFTSDYSKYLDEK*AAKDFIEWLESA-NH₂

H-H-Aib-QGTFTSDYSKYLDSK*AAEDFVEWLESA-NH₂

H-H-Aib-HGTFTSDYSKYLESK*AAEEFIEWLESA-OH

H-HSHGTFTSDYSKYLEEK*AAHEFIEWLESA-OH

H-H-Aib-HGTFTSDYSKYLEEK*AAHEFVEWLESA-NH₂

H-H-Aib-QGTFTSDYSKYLEEK*AAKDFIEWLESA-NH₂

H-H-Aib-QGTFTSDYSKYLESK*AAEDFIEWLESA-NH₂

H-HSQGTFTSDYSKYLEEK*AAKDFIEWLESA-NH₂

H-H-Aib-QGTFTSDYSKYLESK*AAHDFVEWLESA-NH₂

H-H-Aib-QGTFTSDYSKYLESK*AAEDFVEWLESA-NH₂

H-H-DSer-QGTFTSDYSKYLDEK*AAKDFIEWLESA-NH₂
``` or may be a pharmaceutically acceptable salt or solvate thereof.

In certain embodiments, X has the formula:

```
                                              (SEQ ID NO: 1)
H-Aib-QGTFTSDYSKYLDS-K(Hexadecanoyl-isoGlu)-
AAHDFVEWLLS (SEQ ID NO: 2)
HSQGTFTSDYSKYLDS-K(Hexadecanoyl-isoGlu)-
AAHDFVEWLLSA (SEQ ID NO: 4)
H-Aib-QGTFTSDYSKYLDE-K(Hexadecanoyl-isoGlu)-
AAKDFIEWLLSA (SEQ ID NO: 5)
H-Aib-QGTFTSDYSKYLDS-K(Hexadecanoyl-isoGlu)-
AAHDFVEWLESA (SEQ ID NO: 6)
HSQGTFTSDYSRYLDS-K(Hexadecanoyl-isoGlu)-
AAEDFVEWLLRA (SEQ ID NO: 7)
HSQGTFTSDYSKYLDS-K(Hexadecanoyl-isoGlu)-
AAEDFVEWLLRA (SEQ ID NO: 8)
HSQGTFTSDYSKYLDS-K(Hexadecanoyl-isoGlu)-
AAHDFVEWLLS (SEQ ID NO: 9)
HSQGTFTSDYSKYLDS-K(Hexadecanoyl-isoGlu)-
AAHDFVEWLLR (SEQ ID NO: 10)
HSQGTFTSDYSKYLDE-K(Hexadecanoyl-isoGlu)-
AAHEFVEWLESA (SEQ ID NO: 11)
H-Aib-QGTFTSDYSKYLDE-K(Hexadecanoyl-isoGlu)-
RAKDFIEWLLS (SEQ ID NO: 12)
HSQGTFTSDYSRYLDS-K(Hexadecanoyl-isoGlu)-
AAHDFVEWLLSA (SEQ ID NO: 3)
HSQGTFTSDYSKYLDS-K(Hexadecanoyl-isoGlu)-
AAHDFVEWLLRA (SEQ ID NO: 13)
H-Aib-QGTFTSDYSKYLDS-K(Hexadecanoyl-isoGlu)-
AAHDFVEWLLSA (SEQ ID NO: 14)
H-Aib-QGTFTSDYSKYLDE-K(Hexadecanoyl-isoGlu)-
RAKDFIEWLLSA (SEQ ID NO: 15)
H-Aib-QGTFTSDYSKYLDE-K(Hexadecanoyl-isoGlu)-
AAKDFIEWLESA (SEQ ID NO: 16)
H-Aib-QGTFTSDYSKYLDS-K(Hexadecanoyl-isoGlu)-
AAEDFVEWLESA (SEQ ID NO: 17)
H-Aib-HGTFTSDYSKYLES-K(Hexadecanoyl-isoGlu)-
AAEEFIEWLESA (SEQ ID NO: 18)
HSHGTFTSDYSKYLEE-K(Hexadecanoyl-isoGlu)-
AAHEFIEWLESA (SEQ ID NO: 19)
H-Aib-HGTFTSDYSKYLEE-K(Hexadecanoyl-isoGlu)-
AAHEFVEWLESA (SEQ ID NO: 20)
H-Aib-QGTFTSDYSKYLEEK-(Hexadecanoyl-isoGlu)-
AAKDFIEWLESA
```

```
                                                   (SEQ ID NO: 21)
H-Aib-QGTFTSDYSKYLES-K(Hexadecanoyl-isoGlu)-
AAEDFIEWLESA (SEQ ID NO: 22)
HSQGTFTSDYSKYLEE-K(Hexadecanoyl-isoGlu)-
AAKDFIEWLESA (SEQ ID NO: 23)
H-Aib-QGTFTSDYSKYLES-K(Hexadecanoyl-isoGlu)-
AAHDFVEWLESA (SEQ ID NO: 24)
H-Aib-QGTFTSDYSKYLES-K(Hexadecanoyl-isoGlu)-
AAEDFVEWLESA (SEQ ID NO: 25)
H-DSer-QGTFTSDYSKYLDE-K(Hexadecanoyl-isoGlu)-
AAKDFIEWLESA
```

The compound of the invention may be:

```
(Compound 1)
                                                    (SEQ ID NO: 1)
H-H-Aib-QGTFTSDYSKYLDS-K(Hexadecanoyl-isoGlu)-
AAHDFVEWLLS-OH (Compound 2)
                                                    (SEQ ID NO: 2)
H-HSQGTFTSDYSKYLDS-K(Hexadecanoyl-isoGlu)-
AAHDFVEWLLSA-OH (Compound 4)
                                                    (SEQ ID NO: 4)
H-H-Aib-QGTFTSDYSKYLDE-K(Hexadecanoyl-isoGlu)-
AAKDFIEWLLSA-NH (Compound 5)
                                                    (SEQ ID NO: 5)
H-H-Aib-QGTFTSDYSKYLDS-K(Hexadecanoyl-isoGlu)-
AAHDFVEWLESA-NH (Compound 6)
                                                    (SEQ ID NO: 6)
H-HSQGTFTSDYSRYLDS-K(Hexadecanoyl-isoGlu)-
AAEDFIEWLLRA-NH (Compound 7)
                                                    (SEQ ID NO: 7)
H-HSQGTFTSDYSKYLDS-K(Hexadecanoyl-isoGlu)-
AAEDFVEWLLRA-NH (Compound 8)
                                                    (SEQ ID NO: 8)
H-HSQGTFTSDYSKYLDS-K(Hexadecanoyl-isoGlu)-
AAHDFVEWLLS-NH (Compound 9)
                                                    (SEQ ID NO: 9)
H-HSQGTFTSDYSKYLDS-K(Hexadecanoyl-isoGlu)-
AAHDFVEWLLR-OH (Compound 10)
                                                   (SEQ ID NO: 10)
H-HSQGTFTSDYSKYLDE-K(Hexadecanoyl-isoGlu)-
AAHEFVEWLESA-NH (Compound 11)
                                                   (SEQ ID NO: 11)
H-H-Aib-QGTFTSDYSKYLDE-K(Hexadecanoyl-isoGlu)-
RAKDFIEWLLS-OH (Compound 12)
                                                   (SEQ ID NO: 12)
H-HSQGTFTSDYSRYLDS-K(Hexadecanoyl-isoGlu)-
AAHDFVEWLLSA-NH (Compound 3)
                                                    (SEQ ID NO: 3)
H-HSQGTFTSDYSKYLDS-K(Hexadecanoyl-isoGlu)-
AAHDFVEWLLRA-OH (Compound 13)
                                                   (SEQ ID NO: 13)
H-H-Aib-QGTFTSDYSKYLDS-K(Hexadecanoyl-isoGlu)-
AAHDFVEWLLSA-OH (Compound 14)
                                                   (SEQ ID NO: 14)
H-H-Aib-QGTFTSDYSKYLDE-K(Hexadecanoyl-isoGlu)-
RAKDFIEWLLSA-OH (Compound 15)
                                                   (SEQ ID NO: 15)
H-H-Aib-QGTFTSDYSKYLDE-K(Hexadecanoyl-isoGlu)-
AAKDFIEWLESA-NH (Compound 16)
                                                   (SEQ ID NO: 16)
H-H-Aib-QGTFTSDYSKYLDS-K(Hexadecanoyl-isoGlu)-
AAEDFVEWLESA-NH (Compound 17)
                                                   (SEQ ID NO: 17)
H-Aib-HGTFTSDYSKYLES-K(Hexadecanoyl-isoGlu)-
AAEEFIEWLESA-OH (Compound 18)
                                                   (SEQ ID NO: 18)
H-HSHGTFTSDYSKYLEE-K(Hexadecanoyl-isoGlu)-
AAHEFIEWLESA-OH (Compound 19)
                                                   (SEQ ID NO: 19)
H-H-Aib-HGTFTSDYSKYLEE-K(Hexadecanoyl-isoGlu)-
AAHEFVEWLESA-NH (Compound 20)
                                                   (SEQ ID NO: 20)
H-H-Aib-QGTFTSDYSKYLEE-K(Hexadecanoyl-isoGlu)-
AAKDFIEWLESA-NH (Compound 21)
                                                   (SEQ ID NO: 21)
H-H-Aib-QGTFTSDYSKYLES-K(Hexadecanoyl-isoGlu)-
AAEDFIEWLESA-NH (Compound 22)
                                                   (SEQ ID NO: 22)
H-HSQGTFTSDYSKYLEE-K(Hexadecanoyl-isoGlu)-
AAKDFIEWLESA-NH (Compound 23)
                                                   (SEQ ID NO: 23)
H-H-Aib-QGTFTSDYSKYLES-K(Hexadecanoyl-isoGlu)-
AAHDFVEWLESA-NH (Compound 24)
                                                   (SEQ ID NO:24)
H-H-Aib-QGTFTSDYSKYLES-K(Hexadecanoyl-isoGlu)-
AAEDFVEWLESA-NH (Compound 25)
                                                   (SEQ ID NO: 25)
H-H-DSer-QGTFTSDYSKYLDE-K(Hexadecanoyl-isoGlu)-
AAKDFIEWLESA-NH
``` or may be a pharmaceutically acceptable salt or solvate thereof.

or may be a pharmaceutically acceptable salt or solvate thereof.

For those peptide sequences X or X—Z composed exclusively of naturally-occurring amino acids, the invention further provides a nucleic acid (which may be DNA or RNA) encoding a peptide X or X—Z as defined herein. Also provided is an expression vector comprising such a nucleic acid, and a host cell containing such a nucleic acid or expression vector. The host cell is typically capable of expressing and optionally secreting the encoded peptide X or X—Z.

The compounds of the invention are glucagon analogue peptides. References herein to a glucagon analogue peptide should be construed as references to a compound of the invention or to a peptide X or X—Z as the context requires. Reference to a compound of the invention should be taken to include any pharmaceutically acceptable salt (e.g. an acetate or chloride salt) or solvate thereof, unless otherwise stated or excluded by context.

The invention provides a composition comprising a compound of the invention as defined herein (including pharmaceutically acceptable salts or solvates thereof, as already described), a nucleic acid encoding a peptide X or X—Z, an expression vector comprising such a nucleic acid, or a host cell containing such a nucleic acid or expression vector, in admixture with a carrier. In preferred embodiments, the composition is a pharmaceutical composition and the carrier is a pharmaceutically acceptable carrier. The glucagon analogue peptide may be in the form of a pharmaceutically acceptable salt of the glucagon analogue.

The compounds described herein find use, inter alia, in preventing weight gain or promoting weight loss. By "preventing" is meant inhibiting or reducing when compared to the absence of treatment, and is not necessarily meant to imply complete cessation of weight gain. The peptides may cause a decrease in food intake and/or increased energy expenditure, resulting in the observed effect on body weight. Independently of their effect on body weight, the compounds of the invention may have a beneficial effect on glucose control and/or on circulating cholesterol levels, being capable of lowering circulating LDL levels and increasing HDL/LDL ratio. Thus the compounds of the invention can be used for direct or indirect therapy of any condition caused or characterised by excess body weight, such as the treatment and/or prevention of obesity, morbid obesity, obesity linked inflammation, obesity linked gallbladder disease, obesity induced sleep apnea. They may also be used for the prevention of conditions caused or characterised by inadequate glucose control or dyslipidaemia (e.g. elevated LDL levels or reduced HDL/LDL ratio), diabetes (especially Type 2 diabetes), metabolic syndrome, hypertension, atherogenic dyslipidemia, atherosclerosis, arteriosclerosis, coronary heart disease, peripheral artery disease, stroke or microvascular disease. Their effects in these conditions may be as a result of or associated with their effect on body weight, or may be independent thereof.

The invention also provides a compound of the invention for use in a method of medical treatment, particularly for use in a method of treatment of a condition as described above.

The invention also provides the use of a compound of the invention in the preparation of a medicament for the treatment of a condition as described above.

The compound of the invention may be administered as part of a combination therapy with an agent for treatment of diabetes, obesity, dyslipidaemia or hypertension.

In such cases, the two active agents may be given together or separately, and as part of the same pharmaceutical formulation or as separate formulations.

Thus the compound of the invention can be used in combination with an anti-diabetic agent including but not limited to a biguanide (e.g. metformin), a sulfonylurea, a meglitinide or glinide (e.g. nateglinide), a DPP-IV inhibitor, a glitazone, an insulin, or an insulin analogue. Examples of insulin analogues include but are not limited to Lantus™, Novorapid™, Humalog™, Novomix™, Actraphane HM™, Levemir™ and Apidra™.

The compound can further be used in combination with an anti-obesity agent including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

The compound can further be used in combination with an anti-hypertension agent including but not limited to an angiotensin-converting enzyme inhibitor, angiotensin II receptor blocker, diuretic, beta-blocker, or calcium channel blocker.

The compound can be used in combination with an anti-dyslipidaemia agent including but not limited to a statin, a fibrate, a niacin or a cholesterol absorbtion inhibitor.

Thus the invention further provides a composition or therapeutic kit comprising a compound of the invention and for example an anti-diabetic agent, anti-obesity agent, anti-hypertension agent or anti-dyslipidaemia agent as described above. Also provided is such a composition or therapeutic kit for use in a method of medical treatment, especially for treatment of a condition as described above.

The compound of the invention may be made by synthetic chemistry. Accordingly the invention provides a method of synthesis of a compound of the invention.

As already described, the invention extends to nucleic acids encoding the peptide sequence X or X—Z, as well as expression vectors comprising the above-described nucleic acid sequence (optionally operably linked to sequences to direct its expression) and host cells containing the nucleic acids or expression vectors. Preferably the host cells are capable of expressing and optionally secreting the compound of the invention.

The present invention provides a method of producing a compound of the invention, the method comprising culturing the host cells under conditions suitable for expressing the peptide sequence X or X—Z and purifying the compound thus produced. This is particularly useful where the peptide contains only naturally-occurring amino acids.

Where the compound of the invention contains one or more non-naturally-occurring amino acids, the method may comprise expressing a peptide sequence containing one or more differences from the sequence X or X—Z, optionally purifying the compound thus produced, and adding or modifying one or more amino acids to produce a compound of the invention or a compound comprising the amino acid sequence X or X—Z.

Whichever method is used to produce the compound of the invention, it may comprise one or more further steps of modifying the sequence X or X—Z, especially to introduce one or more lipophilic and/or polymeric moieties as defined elsewhere in this specification.

The invention further provides a nucleic acid of the invention, an expression vector of the invention, or a host cell capable of expressing and optionally secreting a compound of the invention, for use in a method of medical treatment. It will be understood that the nucleic acid, expression vector and host cells may be used for treatment of any of the disorders described herein which may be treated with the compounds of the invention themselves. References to a therapeutic composition comprising a compound of the invention, administration of a compound of the invention, or any therapeutic use thereof, should therefore be construed to

DETAILED DESCRIPTION OF THE INVENTION

Throughout this specification, the conventional one letter and three letter codes for naturally occurring amino acids are used, as well as generally accepted three letter codes for other amino acids, such as Aib (α-aminoisobutyric acid), Hse (homoserine), Orn (ornithine), Dbu (2,4-diaminobutyric acid), Dpr (2,3-diaminopropanoic acid).

Glucagon is a 29-amino acid peptide that corresponds to amino acids 53 to 81 of pre-proglucagon and has the sequence His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr (SEQ ID NO: 26). Oxyntomodulin (OXM) is a 37 amino acid peptide which includes the complete 29 amino acid sequence of glucagon with an octapeptide carboxyterminal extension (amino acids 82 to 89 of pre-proglucagon, having the sequence Lys-Arg-Asn-Arg-Asn-Asn-Ile-Ala (SEQ ID NO: 27) and termed "intervening peptide 1" or IP-1; the full sequence of human oxyntomodulin is thus His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-Lys-Arg-Asn-Arg-Asn-Asn-Ile-Ala) (SEQ ID NO: 28). The major biologically active fragment of GLP-1 is produced as a 30-amino acid, C-terminally amidated peptide that corresponds to amino acids 98 to 127 of pre-proglucagon.

The term "native glucagon" thus refers to native human glucagon having the sequence H-His-Ser-Gln-Gly-Thr-Phe-Thr-Ser-Asp-Tyr-Ser-Lys-Tyr-Leu-Asp-Ser-Arg-Arg-Ala-Gln-Asp-Phe-Val-Gln-Trp-Leu-Met-Asn-Thr-OH (SEQ ID NO: 26).

Amino acids within the sequence X of the compounds of the invention can be considered to be numbered consecutively from 1 to 29 in the conventional N-terminal to C-terminal direction. Reference to a "position" within X should be construed accordingly, as should reference to positions within native human glucagon and other molecules.

A compound of the invention may comprise a C-terminal peptide sequence Z of 1-20 amino acids, for example to stabilise the conformation and/or secondary structure of the glucagon analogue peptide, and/or to render the glucagon analogue peptide more resistant to enzymatic hydrolysis, e.g. as described in WO99/46283.

When present, Z represents a peptide sequence of 1-20 amino acid residues, e.g. in the range of 1-15, more preferably in the range of 1-10, in particular in the range of 1-7 amino acid residues, e.g., 1, 2, 3, 4, 5, 6 or 7 amino acid residues, such as 6 amino acid residues. Each of the amino acid residues in the peptide sequence Z may independently be selected from Ala, Leu, Ser, Thr, Tyr, Cys, Glu, Lys, Arg, Dbu (2,4-diaminobutyric acid), Dpr (2,3-diaminopropanoic acid) and Orn (ornithine). Preferably, the amino acid residues are selected from Ser, Thr, Tyr, Glu, Lys, Arg, Dbu, Dpr and Orn, more preferably selected exclusively from Glu, Lys, and Cys. The above-mentioned amino acids may have either D- or L-configuration, which in certain embodiments, have an L-configuration. Particularly preferred sequences Z are sequences of four, five, six or seven consecutive lysine residues (i.e. $Lys_3$, $Lys_4$, $Lys_5$, $Lys_6$ or $Lys_7$), and particularly five or six consecutive lysine residues. Other exemplary sequences of Z are shown in WO 01/04156. Alternatively the C-terminal residue of the sequence Z may be a Cys residue. This may assist in modification (e.g. PEGylation, or conjugation to albumin) of the compound. In such embodiments, the sequence Z may, for example, be only one amino acid in length (i.e. Z=Cys) or may be two, three, four, five, six or even more amino acids in length. The other amino acids therefore serve as a spacer between the peptide X and the terminal Cys residue.

The peptide sequence Z has no more than 25% sequence identity with the corresponding sequence of the IP-1 portion of human OXM (which has the sequence Lys-Arg-Asn-Arg-Asn-Asn-Ile-Ala).

"Percent (%) amino acid sequence identity" of a given peptide or polypeptide sequence with respect to another polypeptide sequence (e.g. IP-1) is calculated as the percentage of amino acid residues in the given peptide sequence that are identical with correspondingly positioned amino acid residues in the corresponding sequence of that other polypeptide when the two are aligned with one another, introducing gaps for optimal alignment if necessary. % identity values may be determined using WU-BLAST-2 (Altschul et al., Methods in Enzymology, 266:460-480 (1996)). WU-BLAST-2 uses several search parameters, most of which are set to the default values. The adjustable parameters are set with the following values: overlap span=1, overlap fraction=0.125, word threshold (T)=11. A % amino acid sequence identity value is determined by the number of matching identical residues as determined by WU-BLAST-2, divided by the total number of residues of the reference sequence (gaps introduced by WU-BLAST-2 into the reference sequence to maximize the alignment score being ignored), multiplied by 100.

Thus, when Z is aligned optimally with the 8 amino acids of IP-1, it has no more than two amino acids which are identical with the corresponding amino acids of IP-1.

In certain embodiments, Z is absent.

One or more of the amino acid side chains in the compound of the invention may be conjugated to a lipophilic substituent. The lipophilic substituent may be covalently bonded to an atom in the amino acid side chain, or alternatively may be conjugated to the amino acid side chain by a spacer. A lipophilic substituent may be conjugated to a side chain of an amino acid which is part of the peptide X, and/or to a side chain of an amino acid which is part of the peptide Z.

Without wishing to be bound by any particular theory, it is thought that the lipophilic substituent binds albumin in the blood stream, thus shielding the compounds of the invention from enzymatic degradation and thereby enhancing the half-life of the compounds. It may also modulate the potency of the compound, e.g. with respect to the glucagon receptor and/or the GLP-1 receptor.

In certain embodiments, only one amino acid side chain is conjugated to a lipophilic substituent. In other embodiments, two amino acid side chains are each conjugated to a lipophilic substituent. In yet further embodiments, three or even more amino acid side chains are each conjugated to a lipophilic substituent. When a compound contains two or more lipophilic substituents, they may be the same or different.

The lipophilic substituent may comprise or consist of a lipophilic moiety $Z^1$ which may be covalently bonded directly to an atom in the amino acid side chain, or alternatively may be conjugated to the amino acid side chain by a spacer $Z^2$.

The term "conjugated" is used here to describe the physical attachment of one identifiable chemical moiety to another, and the structural relationship between such moieties. It should not be taken to imply any particular method of synthesis.

The lipophilic moiety may be attached to the amino acid side chain or to the spacer via an ester, a sulphonyl ester, a thioester, an amide, a carbamate, a urea or a sulphonamide. Accordingly it will be understood that preferably the lipophilic substituent includes an acyl group, a sulphonyl group, an N atom, an O atom or an S atom which forms part of the ester, sulphonyl ester, thioester, amide or sulphonamide. Preferably, an acyl group in the lipophilic substituent forms part of an amide or ester with the amino acid side chain or the spacer.

The lipophilic moiety may include a hydrocarbon chain having 4 to 30 C atoms. Preferably it has at least 8 or 12 C atoms, and preferably it has 24 C atoms or fewer, or 20 C atoms or fewer. The hydrocarbon chain may be linear or branched and may be saturated or unsaturated. It will be understood that the hydrocarbon chain is preferably substituted with a moiety which forms part of the attachment to the amino acid side chain or the spacer, for example an acyl group, a sulphonyl group, an N atom, an O atom or an S atom. Most preferably the hydrocarbon chain is substituted with acyl, and accordingly the hydrocarbon chain may be part of an alkanoyl group, for example palmitoyl, caproyl, lauroyl, myristoyl or stearoyl.

Accordingly, the lipophilic moiety may have the formula shown below:

A may be, for example, an acyl group, a sulphonyl group, NH, N-alkyl, an O atom or an S atom, preferably acyl. n is an integer from 3 to 29, preferably from 7 to 25, more preferred 11 to 21, even more preferred 15 to 19.

The hydrocarbon chain may be further substituted. For example, it may be further substituted with up to three substituents selected from $NH_2$, OH and COOH, especially at the free end of the molecule distal from the spacer or peptide. For example, it may comprise a free carboxylic acid group.

If the hydrocarbon chain is further substituted, preferably it is further substituted with only one substituent. Alternatively or additionally, the hydrocarbon chain may include a cycloalkane or heterocycloalkane, for example as shown below:

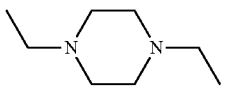

Preferably the cycloalkane or heterocycloalkane is a six-membered ring. Most preferably, it is piperidine.

Alternatively, the lipophilic moiety may be based on a cyclopentanophenanthrene skeleton, which may be partially or fully unsaturated, or saturated. The carbon atoms in the skeleton each may be substituted with Me or OH. For example, the lipophilic substituent may be cholyl, deoxycholyl or lithocholyl.

As mentioned above, the lipophilic moiety may be conjugated to the amino acid side chain by a spacer. When present, the spacer is attached to the lipophilic moiety and to the amino acid side chain. The spacer may be attached to the lipophilic moiety and to the amino acid side chain independently by an ester, a sulphonyl ester, a thioester, an amide, a carbamate, a urea or a sulphonamide. Accordingly, it may include two moieties independently selected from acyl, sulphonyl, an N atom, an O atom or an S atom. The spacer may have the formula:

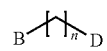

wherein B and D are each independently selected from acyl, sulphonyl, NH, N-alkyl, an O atom and an S atom, preferably from acyl and NH. Preferably, n is an integer from 1 to 10, preferably from 1 to 5. The spacer may be further substituted with one or more substituents selected from $C_{0-6}$ alkyl, $C_{0-6}$ alkyl amine, $C_{0-6}$ alkyl hydroxy and $C_{0-6}$ alkyl carboxy.

Alternatively, the spacer may have two or more repeat units of the formula above. B, D and n are each selected independently for each repeat unit. Adjacent repeat units may be covalently attached to each other via their respective B and D moieties. For example, the B and D moieties of the adjacent repeat units may together form an ester, a sulphonyl ester, a thioester, an amide or a sulphonamide. The free B and D units at each end of the spacer are attached to the amino acid side chain and the lipophilic moiety as described above.

Preferably the spacer has five or fewer, four or fewer or three or fewer repeat units. Most preferably the spacer has two repeat units, or is a single unit.

The spacer (or one or more of the repeat units of the spacer, if it has repeat units) may be, for example, a natural or unnatural amino acid. It will be understood that for amino acids having functionalised side chains, B and/or D may be a moiety within the side chain of the amino acid. The spacer may be any naturally occurring or unnatural amino acid. For example, the spacer (or one or more of the repeat units of the spacer, if it has repeat units) may be Gly, Pro, Ala, Val, Leu, Ile, Met, Cys, Phe, Tyr, Trp, His, Lys, Arg, Gln, Asn, α-Glu, γ-Glu, Asp, Ser Thr, Gaba, Aib, β-Ala, 5-aminopentanoyl, 6-aminohexanoyl, 7-aminoheptanoyl, 8-aminooctanoyl, 9-aminononanoyl or 10-aminodecanoyl.

For example, the spacer may be a single amino acid selected from γ-Glu, Gaba, β-Ala and α-Glu.

A lipophilic substituent may be conjugated to any amino acid side chain in a compound of the invention. Preferably, the amino acid side chain includes a carboxy, hydroxyl, thiol, amide or amine group, for forming an ester, a sulphonyl ester, a thioester, an amide or a sulphonamide with the spacer or lipophilic substituent. For example, the lipophilic substituent may be conjugated to Asn, Asp, Glu, Gln, His, Lys, Arg, Ser, Thr, Tyr, Trp, Cys or Dbu, Dpr or Orn. Preferably, the lipophilic substituent is conjugated to Lys. An amino acid shown as Lys in the formulae provided herein may be replaced by, e.g., Dbu, Dpr or Orn where a lipophilic substituent is added.

An example of a lipophilic substituent comprising lipophilic moiety and spacer is shown in the formula below:

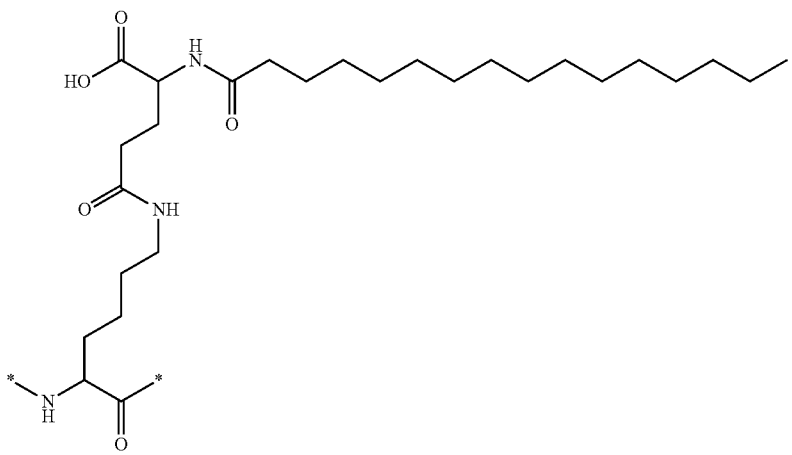 [SMILES: *NC(CCCCNC(=O)CCC(NC(=O)CCCCCCCCCCCCCCC)C(=O)O)C(*)=O]

Here, a Lys residue in the compound of the present invention is covalently attached to γ-Glu (the spacer) via an amide moiety. Palmitoyl (i.e. hexadecanoyl) is covalently attached to the γ-Glu spacer via an amide moiety, thus creating a hexadecanoyl-isoGlu group.

Alternatively or additionally, one or more amino acid side chains in the compound of the invention may be conjugated to a polymeric moiety, for example, in order to increase solubility and/or half-life in vivo (e.g. in plasma) and/or bioavailability. Such modification is also known to reduce clearance (e.g. renal clearance) of therapeutic proteins and peptides.

The skilled reader will be well aware of suitable techniques that can be used to perform the coupling reactions with spacer and lipophilic moiety using general synthetic methodology listed e.g. in "Comprehensive Organic Transformations, A Guide to Functional Group Preparations", 2nd edition, Larock, R. C.; Wiley-VCH: New York, 1999. Such transformations may take place at any suitable stage during the synthesis process.

The polymeric moiety is preferably water-soluble (amphiphilic or hydrophilic), non-toxic, and pharmaceutically inert. Suitable polymeric moieties include polyethylene glycol (PEG), homo- or co-polymers of PEG, a monomethyl-substituted polymer of PEG (mPEG), and polyoxyethylene glycerol (POG). See, for example, *Int. J. Hematology* 68:1 (1998); *Bioconjugate Chem.* 6:150 (1995); and *Crit. Rev. Therap. Drug Carrier Sys.* 9:249 (1992).

Other suitable polymeric moieties include poly-amino acids such as poly-lysine, poly-aspartic acid and poly-glutamic acid (see for example Gombotz, et al. (1995), Bioconjugate Chem., vol. 6: 332-351; Hudecz, et al. (1992), Bioconjugate Chem., vol. 3, 49-57; Tsukada, et al. (1984), J. Natl. Cancer Inst., vol 73: 721-729; and Pratesi, et al. (1985), Br. J. Cancer, vol. 52: 841-848).

The polymeric moiety may be straight-chain or branched. It may have a molecular weight of 500-40,000 Da, for example 500-10,000 Da, 1000-5000 Da, 10,000-20,000 Da, or 20,000-40,000 Da.

A compound of the invention may comprise two or more such moieties, in which case the total molecular weight of all such moieties will generally fall within the ranges provided above.

The polymeric moiety may be coupled (by covalent linkage) to an amino, carboxyl or thiol group of an amino acid side chain. Preferred examples are the thiol group of Cys residues and the epsilon amino group of Lys residues. The carboxyl groups of Asp and Glu residues may also be used.

The skilled reader will be well aware of suitable techniques that can be used to perform the coupling reaction. For example, a PEG moiety carrying a methoxy group can be coupled to a Cys thiol group by a maleimido linkage using reagents commercially available from Nektar Therapeutics. See also WO 2008/101017, and the references cited above, for details of suitable chemistry.

Peptide Synthesis

The compounds of the present invention may be manufactured either by standard synthetic methods, recombinant expression systems, or any other state of the art method. Thus the glucagon analogues may be synthesised in a number of ways, including, for example, a method which comprises:

(a) synthesizing the peptide by means of solid-phase or liquid-phase methodology, either stepwise or by fragment assembly, and isolation and purifying of the final peptide product; or (b) expressing a nucleic acid construct that encodes the peptide in a host cell, and recovering the expression product from the host cell or culture medium; or (c) effecting cell-free in vitro expression of a nucleic acid construct that encodes the peptide, and recovering the expression product;

or any combination of methods of (a), (b), and (c) to obtain fragments of the peptide, subsequently ligating the fragments to obtain the peptide, and recovering the peptide.

It is preferred to synthesize the analogues of the invention by means of solid-phase or liquid-phase peptide synthesis. In this context, reference is made to WO 98/11125 and, among many others, Fields, G B et al., 2002, "Principles and practice of solid-phase peptide synthesis". In: Synthetic Peptides (2nd Edition), and the Examples herein.

For recombinant expression, the nucleic acid fragments of the invention will normally be inserted in suitable vectors to form cloning or expression vectors carrying the nucleic acid fragments of the invention; such novel vectors are also part of the invention. The vectors can, depending on purpose and type of application, be in the form of plasmids, phages, cosmids, mini-chromosomes, or virus, but also naked DNA which is only expressed transiently in certain cells is an important vector. Preferred cloning and expression vectors (plasmid vectors) of the invention are capable of autonomous replication, thereby enabling high copy-numbers for the purposes of high-level expression or high-level replication for subsequent cloning.

In general outline, an expression vector comprises the following features in the 5'→3' direction and in operable linkage: a promoter for driving expression of the nucleic acid fragment of the invention, optionally a nucleic acid sequence encoding a leader peptide enabling secretion (to the extracellular phase or, where applicable, into the periplasma), the nucleic acid fragment encoding the peptide of the invention, and optionally a nucleic acid sequence encoding a terminator. They may comprise additional features such as selectable markers and origins of replication. When operating with expression vectors in producer strains or cell lines it may be preferred that the vector is capable of integrating into the host cell genome. The skilled person is very familiar with suitable vectors and is able to design one according to their specific requirements.

The vectors of the invention are used to transform host cells to produce the compound of the invention. Such transformed cells, which are also part of the invention, can be cultured cells or cell lines used for propagation of the nucleic acid fragments and vectors of the invention, or used for recombinant production of the peptides of the invention.

Preferred transformed cells of the invention are microorganisms such as bacteria [such as the species *Escherichia* (e.g. *E. coli*), *Bacillus* (e.g. *Bacillus subtilis*), *Salmonella*, or *Mycobacterium* (preferably non-pathogenic, e.g. *M. bovis* BCG), yeasts (e.g., *Saccharomyces cerevisiae* and *Pichia pastoris*), and protozoans. Alternatively, the transformed cells may be derived from a multicellular organism, i.e. it may be fungal cell, an insect cell, an algal cell, a plant cell, or an animal cell such as a mammalian cell. For the purposes of cloning and/or optimised expression it is preferred that the transformed cell is capable of replicating the nucleic acid fragment of the invention. Cells expressing the nucleic fragment are useful embodiments of the invention; they can be used for small-scale or large-scale preparation of the peptides of the invention.

When producing the peptide of the invention by means of transformed cells, it is convenient, although far from essential, that the expression product is secreted into the culture medium.

Efficacy

Binding of the relevant compounds to GLP-1 or glucagon (Glu) receptors may be used as an indication of agonist activity, but in general it is preferred to use a biological assay which measures intracellular signalling caused by binding of the compound to the relevant receptor. For example, activation of the glucagon receptor by a glucagon agonist will stimulate cellular cyclic AMP (cAMP) formation. Similarly, activation of the GLP-1 receptor by a GLP-1 agonist will stimulate cellular cAMP formation. Thus, production of cAMP in suitable cells expressing one of these two receptors can be used to monitor the relevant receptor activity. Use of a suitable pair of cell types, each expressing one receptor but not the other, can hence be used to determine agonist activity towards both types of receptor.

The skilled person will be aware of suitable assay formats, and examples are provided below. The GLP-1 receptor and/or the glucagon receptor may have the sequence of the receptors as described in the examples. For example, the assays may employ the human glucagon receptor (Glucagon-R) having primary accession number GI:4503947 and/or the human glucagon-like peptide 1 receptor (GLP-1R) having primary accession number GI:166795283. (in that where sequences of precursor proteins are referred to, it should of course be understood that assays may make use of the mature protein, lacking the signal sequence).

$EC_{50}$ values may be used as a numerical measure of agonist potency at a given receptor. An $EC_{50}$ value is a measure of the concentration of a compound required to achieve half of that compound's maximal activity in a particular assay. Thus, for example, a compound having $EC_{50}$[GLP-1] lower than the $EC_{50}$[GLP-1] of glucagon in a particular assay may be considered to have higher GLP-1 receptor agonist potency than glucagon.

The compounds described in this specification are typically GluGLP-1 dual agonists, as determined by the observation that they are capable of stimulating cAMP formation at both the glucagon receptor and the GLP-1 receptor. The stimulation of each receptor can be measured in independent assays and afterwards compared to each other.

By comparing the $EC_{50}$ value for the GLP-1 receptor ($EC_{50}$ [GLP-1-R]) with the $EC_{50}$ value for the Glucagon receptor, ($EC_{50}$ [GlucagonR]) for a given compound. the relative GLP-1R selectivity can be calculated as follows:

Relative GLP-1R selectivity [compound]=($EC_{50}$[GLP-1R])/($EC_{50}$[Glucagon-R])

The term "$EC_{50}$" stands for the half maximal Effective Concentration, typically at a particular receptor, or on the level of a particular marker for receptor function, and can refer to an inhibitory or an antagonistic activity, depending on the specific biochemical context.

Without wishing to be bound by any particular theory, a compound's relative selectivity may allow its effect on the GLP-1 or glucagon receptor to be compared directly to its effect on the other receptor. For example, the higher a compound's relative GLP-1 selectivity is, the more effective that compound may be on the GLP-1 receptor as compared to the glucagon receptor. Typically the results are compared for glucagon and GLP-1 receptors from the same species, e.g. human glucagon and GLP-1 receptors, or murine glucagon and GLP-1 receptors.

The compounds of the invention may have a higher relative GLP-1R selectivity than human glucagon in that for a particular level of glucagon-R agonist activity, the compound may display a higher level of GLP-1R agonist activity (i.e. greater potency at the GLP-1 receptor) than glucagon. It will be understood that the absolute potency of a particular compound at the glucagon and GLP-1 receptors may be higher, lower or approximately equal to that of native human glucagon, as long as the appropriate relative GLP-1R selectivity is achieved.

Nevertheless, the compounds of this invention may have a lower $EC_{50}$ [GLP-1R] than human glucagon. The compounds may have a lower $EC_{50}$[GLP-1-R] than glucagon while maintaining an $EC_{50}$ [Glucagon-R] that is less than 10-fold higher than that of human glucagon, less than 5-fold higher than that of human glucagon, or less than 2-fold higher than that of human glucagon.

The compounds of the invention may have an $EC_{50}$ [Glucagon-R] that is less than two-fold that of human glucagon. The compounds may have an $EC_{50}$ [Glucagon-R] that is less than two-fold that of human glucagon and have an $EC_{50}$ [GLP-1R] that is less than half that of human glucagon, less than a fifth of that of human glucagon, or less than a tenth of that of human glucagon.

The relative GLP-1R selectivity of the compounds may be between 0.05 and 20. For example, the compounds may have a relative selectivity of 0.05-0.20, 0.1-0.30, 0.2-0.5, 0.3-0.7, or 0.5-1.0; 1.0-2.0, 1.5-3.0, 2.0-4.0 or 2.5-5.0; or 0.05-20, 0.075-15, 0.1-10, 0.15-5, 0.75-2.5 or 0.9-1.1.

In certain embodiments, it may be desirable that $EC_{50}$ of any given compound for both the Glucagon-R and GLP-1R, e.g. for the human glucagon and GLP-1 receptors, should be less than 1 nM.

Therapeutic Uses

The compounds of the invention may provide attractive treatment and/or prevention options for, inter alia, obesity and metabolic diseases including diabetes, as discussed below.

Diabetes comprises a group of metabolic diseases characterized by hyperglycemia resulting from defects in insulin secretion, insulin action, or both. Acute signs of diabetes include excessive urine production, resulting compensatory thirst and increased fluid intake, blurred vision, unexplained weight loss, lethargy, and changes in energy metabolism. The chronic hyperglycemia of diabetes is associated with long-term damage, dysfunction, and failure of various organs, notably the eyes, kidneys, nerves, heart and blood vessels. Diabetes is classified into type 1 diabetes, type 2 diabetes and gestational diabetes on the basis on pathogenetic characteristics.

Type 1 diabetes accounts for 5-10% of all diabetes cases and is caused by auto-immune destruction of insulin-secreting pancreatic β-cells.

Type 2 diabetes accounts for 90-95% of diabetes cases and is a result of a complex set of metabolic disorders. Type 2 diabetes is the consequence of endogenous insulin production becoming insufficient to maintain plasma glucose levels below the diagnostic thresholds.

Gestational diabetes refers to any degree of glucose intolerance identified during pregnancy.

Pre-diabetes includes impaired fasting glucose and impaired glucose tolerance and refers to those states that occur when blood glucose levels are elevated but below the levels that are established for the clinical diagnosis for diabetes.

A large proportion of people with type 2 diabetes and pre-diabetes are at increased risk of morbidity and mortality due to the high prevalence of additional metabolic risk factors including abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension) a prothrombotic state (e.g. high fibrinogen or plasminogen activator inhibitor—1 in the blood), and proinflammatory state (e.g., elevated C-reactive protein in the blood).

Conversely, obesity confers an increased risk of developing pre-diabetes, type 2 diabetes as well as e.g. certain types of cancer, obstructive sleep apnea and gall-bladder disease.

Dyslipidaemia is associated with increased risk of cardiovascular disease. High Density Lipoprotein (HDL) is of clinical importance since an inverse correlation exists between plasma HDL concentrations and risk of atherosclerotic disease. The majority of cholesterol stored in atherosclerotic plaques originates from LDL and hence elevated concentrations Low Density Lipoproteins (LDL) is closely associated with atherosclerosis. The HDL/LDL ratio is a clinical risk indictor for atherosclerosis and coronary atherosclerosis in particular.

Metabolic syndrome is characterized by a group of metabolic risk factors in one person. They include abdominal obesity (excessive fat tissue around the abdominal internal organs), atherogenic dyslipidemia (blood fat disorders including high triglycerides, low HDL cholesterol and/or high LDL cholesterol, which foster plaque buildup in artery walls), elevated blood pressure (hypertension), insulin resistance and glucose intolerance, prothrombotic state (e.g. high fibrinogen or plasminogen activator inhibitor-1 in the blood), and proinflammatory state (e.g., elevated C-reactive protein in the blood).

Individuals with the metabolic syndrome are at increased risk of coronary heart disease and other diseases related to other manifestations of arteriosclerosis (e.g., stroke and peripheral vascular disease). The dominant underlying risk factors for this syndrome appear to be abdominal obesity.

Without wishing to be bound by any particular theory, it is believed that the compounds of the invention act as dual agonists both on the human glucagon-receptor and the human GLP1-receptor, abbreviated here as dual GluGLP-1 agonists. The dual agonist may combine the effect of glucagon, e.g. on fat metabolism, with the effect of GLP-1, e.g. on blood glucose levels and food intake. They may therefore act to accelerate elimination of excessive adipose tissue, induce sustainable weight loss, and improve glycaemic control. Dual GluGLP-1 agonists may also act to reduce cardiovascular risk factors such as high cholesterol, high LDL-cholesterol or low HDL/LDL cholesterol ratios.

The compounds of the present invention can therefore be used in a subject in need thereof as pharmaceutical agents for preventing weight gain, promoting weight loss, reducing excess body weight or treating obesity (e.g. by control of appetite, feeding, food intake, calorie intake, and/or energy expenditure), including morbid obesity, as well as associated diseases and health conditions including but not limited to obesity linked inflammation, obesity linked gallbladder disease and obesity induced sleep apnea. The compounds of the invention may also be used for treatment of conditions caused by or associated with impaired glucose control, including metabolic syndrome, insulin resistance, glucose intolerance, pre-diabetes, increased fasting glucose, type 2 diabetes, hypertension, atherosclerois, arteriosclerosis, coronary heart disease, peripheral artery disease and stroke, in a subject in need thereof. Some of these conditions can be associated with obesity. However, the effects of the compounds of the invention on these conditions may be mediated in whole or in part via an effect on body weight, or may be independent thereof.

The synergistic effect of dual GluGLP-1 agonists may also result in reduction of cardiovascular risk factors such as high cholesterol and LDL, which may be entirely independent of their effect on body weight.

Thus the invention provides the use of a compound of the invention in the treatment of a condition as described above, in an individual in need thereof.

The invention also provides a compound of the invention for use in a method of medical treatment, particularly for use in a method of treatment of a condition as described above.

In a preferred aspect, the compounds described may be used in treating diabetes, esp. type 2 diabetes.

In a specific embodiment, the present invention comprises use of a compound for treating diabetes, esp. type 2 diabetes in an individual in need thereof.

In a not less preferred aspect, the compounds described may be used in preventing weight gain or promoting weight loss.

In a specific embodiment, the present invention comprises use of a compound for preventing weight gain or promoting weight loss in an individual in need thereof.

In a specific embodiment, the present invention comprises use of a compound in a method of treatment of a condition caused or characterised by excess body weight, e.g. the treatment and/or prevention of obesity, morbid obesity, morbid obesity prior to surgery, obesity linked inflammation, obesity linked gallbladder disease, obesity induced sleep apnea, prediabetes, diabetes, esp. type 2 diabetes, hypertension, atherogenic dyslipidimia, atherosclerois, arteriosclerosis, coronary heart disease, peripheral artery disease, stroke or microvascular disease in an individual in need thereof.

In another aspect, the compounds described may be used in a method of lowering circulating LDL levels, and/or increasing HDL/LDL ratio.

In a specific embodiment, the present invention comprises use of a compound in a method of lowering circulating LDL levels, and/or increasing HDL/LDL ratio in an individual in need thereof.

In another aspect, the compounds described may be used in a method of lowering circulating triglyceride levels.

Pharmaceutical Compositions

The compounds of the present invention may be formulated as pharmaceutical compositions prepared for storage or administration. Such a composition typically comprises a therapeutically effective amount of a compound of the invention, in the appropriate form, in a pharmaceutically acceptable carrier.

The therapeutically effective amount of a compound of the present invention will depend on the route of administration, the type of mammal being treated, and the physical characteristics of the specific mammal under consideration. These factors and their relationship to determining this amount are well known to skilled practitioners in the medical arts. This amount and the method of administration can be tailored to achieve optimal efficacy, and may depend on such factors as weight, diet, concurrent medication and other factors, well known to those skilled in the medical arts. The dosage sizes and dosing regimen most appropriate for human use may be guided by the results obtained by the present invention, and may be confirmed in properly designed clinical trials. The compounds of the present invention may be particularly useful for treatment of humans.

An effective dosage and treatment protocol may be determined by conventional means, starting with a low dose in laboratory animals and then increasing the dosage while monitoring the effects, and systematically varying the dosage regimen as well. Numerous factors may be taken into consideration by a clinician when determining an optimal dosage for a given subject. Such considerations are known to the skilled person.

The term "pharmaceutically acceptable carrier" includes any of the standard pharmaceutical carriers. Pharmaceutically acceptable carriers for therapeutic use are well known in the pharmaceutical art, and are described, for example, in Remington's Pharmaceutical Sciences, Mack Publishing Co. (A. R. Gennaro edit. 1985). For example, sterile saline and phosphate-buffered saline at slightly acidic or physiological pH may be used. pH buffering agents may be phosphate, citrate, acetate, tris/hydroxymethyl)aminomethane (TRIS), N-Tris(hydroxymethyl)methyl-3-aminopropanesulphonic acid (TAPS), ammonium bicarbonate, diethanolamine, histidine, which is a preferred buffer, arginine, lysine, or acetate or mixtures thereof. The term further encompasses any agents listed in the US Pharmacopeia for use in animals, including humans.

The term "pharmaceutically acceptable salt" refers to a salt of any one of the compounds of the invention. Salts include pharmaceutically acceptable salts such as acid addition salts and basic salts. Examples of acid addition salts include hydrochloride salts, citrate salts and acetate salts.

Examples of basic salts include salts where the cation is selected from alkali metals, such as sodium and potassium, alkaline earth metals, such as calcium, and ammonium ions $^+N(R^3)_3(R^4)$, where $R^3$ and $R^4$ independently designates optionally substituted $C_{1-6}$-alkyl, optionally substituted $C_{2-6}$-alkenyl, optionally substituted aryl, or optionally substituted heteroaryl. Other examples of pharmaceutically acceptable salts are described in "Remington's Pharmaceutical Sciences", 17th edition. Ed. Alfonso R. Gennaro (Ed.), Mark Publishing Company, Easton, Pa., U.S.A., 1985 and more recent editions, and in the Encyclopaedia of Pharmaceutical Technology.

"Treatment" is an approach for obtaining beneficial or desired clinical results. For the purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures in certain embodiments. Those in need of treatment include those already with the disorder as well as those in which the disorder is to be prevented. By treatment is meant inhibiting or reducing an increase in pathology or symptoms (e.g. weight gain, hyperglycemia) when compared to the absence of treatment, and is not necessarily meant to imply complete cessation of the relevant condition.

The pharmaceutical compositions can be in unit dosage form. In such form, the composition is divided into unit doses containing appropriate quantities of the active component. The unit dosage form can be a packaged preparation, the package containing discrete quantities of the preparations, for example, packeted tablets, capsules, and powders in vials or ampoules. The unit dosage form can also be a capsule, cachet, or tablet itself, or it can be the appropriate number of any of these packaged forms. It may be provided in single dose injectable form, for example in the form of a pen. In certain embodiments, packaged forms include a label or insert with instructions for use. Compositions may be formulated for any suitable route and means of administration. Pharmaceutically acceptable carriers or diluents include those used in formulations suitable for oral, rectal, nasal, topical (including buccal and sublingual), vaginal or parenteral (including subcutaneous, intramuscular, intravenous, intradermal, and transdermal) administration. The formulations may conveniently be presented in unit dosage form and may be prepared by any of the methods well known in the art of pharmacy.

Subcutaneous or transdermal modes of administration may be particularly suitable for the compounds described herein.

Compositions of the invention may further be compounded in, or attached to, for example through covalent, hydrophobic and electrostatic interactions, a drug carrier, drug delivery system and advanced drug delivery system in order to further enhance stability of the compound, increase bioavailability, increase solubility, decrease adverse effects, achieve chronotherapy well known to those skilled in the art, and increase patient compliance or any combination thereof. Examples of carriers, drug delivery systems and advanced drug delivery systems include, but are not limited to, polymers, for example cellulose and derivatives, polysaccharides, for example dextran and derivatives, starch and derivatives, poly(vinyl alcohol), acrylate and methacrylate polymers, polylactic and polyglycolic acid and block co-polymers thereof, polyethylene glycols, carrier proteins, for example albumin, gels, for example, thermogelling systems, for example block co-polymeric systems well known to those skilled in the art, micelles, liposomes, microspheres, nanoparticulates, liquid crystals and dispersions thereof, L2 phase and dispersions there of, well known to those skilled in the art of phase behaviour in lipid-water systems, polymeric micelles, multiple emulsions, self-emulsifying, self-microemulsifying, cyclodextrins and derivatives thereof, and dendrimers.

Combination Therapy

A compound or composition of the invention may be administered as part of a combination therapy with an agent for treatment of obesity, hypertension, dyslipidemia or diabetes.

In such cases, the two active agents may be given together or separately, and as part of the same pharmaceutical formulation or as separate formulations.

Thus a compound or composition of the invention can further be used in combination with an anti-obesity agent, including but not limited to a glucagon-like peptide receptor 1 agonist, peptide YY or analogue thereof, cannabinoid receptor 1 antagonist, lipase inhibitor, melanocortin receptor 4 agonist, or melanin concentrating hormone receptor 1 antagonist.

A compound or composition of the invention can be used in combination with an anti-hypertension agent, including but not limited to an angiotensin-converting enzyme inhibitor, angiotensin II receptor blocker, diuretics, beta-blocker, or calcium channel blocker.

A compound or composition of the invention can be used in combination with a dyslipidaemia agent, including but not limited to a statin, a fibrate, a niacin and/or a cholesterol absorbtion inhibitor.

Further, a compound or composition of the invention can be used in combination with an anti-diabetic agent, including but not limited to a biguanide (e.g. metformin), a sulfonylurea, a meglitinide or glinide (e.g. nateglinide), a DPP-IV inhibitor, a glitazone, a different GLP-1 agonist, an insulin or an insulin analogue. In a preferred embodiment, the compound or salt thereof is used in combination with insulin or an insulin analogue, DPP-IV inhibitor, sulfonylurea or metformin, particularly sulfonylurea or metformin, for achieving adequate glycemic control. Examples of insulin analogues include but are not limited to Lantus, Novorapid, Humalog, Novomix, and Actraphane HM, Levemir and Apidra.

EXAMPLES

Example 1: General Synthesis of Glucagon Analogues

Solid phase peptide synthesis (SPPS) was performed on a microwave assisted synthesizer using standard Fmoc strategy in NMP on a polystyrene resin (TentaGel S Ram). HATU was used as coupling reagent together with DIPEA as base. Piperidine (20% in NMP) was used for deprotection. Pseudoprolines: Fmoc-Phe-Thr(psiMe,Mepro)-OH and Fmoc-Asp-Ser(psiMe,Mepro)-OH (purchased from NovaBiochem) were used where applicable.

Abbreviations employed are as follows:
Boc: tert-butyloxycarbonyl
ivDde: 1-(4,4-dimethyl-2,6-dioxocyclohexylidene)3-methyl-butyl
Dde: 1-(4,4-dimethyl-2,6-dioxocyclohexylidene)-ethyl
DCM: dichloromethane
DMF: N,N-dimethylformamide
DIPEA: diisopropylethylamine
EDT: 1,2-ethanedithiol
EtOH: ethanol
Et$_2$O: diethyl ether
HATU: N-[(dimethylamino)-1H-1,2,3-triazol[4,5-b]pyridine-1-ylmethylene]-N-methylmethanaminium hexafluorophosphate N-oxide
MeCN: acetonitrile
NMP: N-methylpyrrolidone
TFA: trifluoroacetic acid
TIS: triisopropylsilane Cleavage:

The crude peptide was cleaved from the resin by treatment with 95/2.5/2.5% (v/v) TFA/TIS/water at room temperature (r.t.) for 2 hours. For peptides with a methionine in the sequence a mixture of 95/5 (v/v) TFA/EDT was used. Most of the TFA was removed at reduced pressure and the crude peptide was precipitated and washed with diethylether and allowed to dry to constant weight at ambient temperature.

The following compounds were synthesised:

```
(Compound 1)
H-H-Aib-QGTFTSDYSKYLDS-K(Hexadecanoyl-isoGlu)-
AAHDFVEWLLS-OH (Compound 2)
H-HSQGTFTSDYSKYLDS-K(Hexadecanoyl-isoGlu)-
AAHDFVEWLLSA-OH (Compound 3)
H-HSQGTFTSDYSKYLDS-K(Hexadecanoyl-isoGlu)-
AAHDFVEWLLRA-OH (Compound 4)
H-H-Aib-QGTFTSDYSKYLDE-K(Hexadecanoyl-isoGlu)-
AAKDFIEWLLSA-NH$_2$ (Compound 5)
H-H-Aib-QGTFTSDYSKYLDS-K(Hexadecanoyl-isoGlu)-
AAHDFVEWLESA-NH$_2$ (Compound 6)
H-HSQGTFTSDYSRYLDS-K(Hexadecanoyl-isoGlu)-
AAEDFVEWLLRA-NH$_2$ (Compound 7)
H-HSQGTFTSDYSKYLDS-K(Hexadecanoyl-isoGlu)-
AAEDFVEWLLRA-NH$_2$ (Compound 8)
H-HSQGTFTSDYSKYLDS-K(Hexadecanoyl-isoGlu)-
AAHDFVEWLLS-NH$_2$ (Compound 9)
H-HSQGTFTSDYSKYLDS-K(Hexadecanoyl-isoGlu)-
AAHDFVEWLLR-OH (Compound 10)
H-HSQGTFTSDYSKYLDE-K(Hexadecanoyl-isoGlu)-
AAHEFVEWLESA-NH$_2$ (Compound 11)
H-H-Aib-QGTFTSDYSKYLDE-K(Hexadecanoyl-isoGlu)-
RAKDFIEWLLS-OH
```

-continued (Compound 12)
H-HSQGTFTSDYSRYLDS-K(Hexadecanoyl-isoGlu)-
AAHDFVEWLLSA-NH$_2$ (Compound 13)
H-H-Aib-QGTFTSDYSKYLDS-K(Hexadecanoyl-isoGlu)-
AAHDFVEWLLSA-OH (Compound 14)
H-H-Aib-QGTFTSDYSKYLDE-K(Hexadecanoyl-isoGlu)-
RAKDFIEWLLSA-OH (Compound 15)
H-H-Aib-QGTFTSDYSKYLDE-K(Hexadecanoyl-isoGlu)-
AAKDFIEWLESA-NH$_2$ (Compound 16)
H-H-Aib-QGTFTSDYSKYLDS-K(Hexadecanoyl-isoGlu)-
AAEDFVEWLESA-NH$_2$ (Compound 17)
H-H-Aib-HGTFTSDYSKYLES-K(Hexadecanoyl-isoGlu)-
AAEEFIEWLESA-OH (Compound 18)
H-HSHGTFTSDYSKYLEE-K(Hexadecanoyl-isoGlu)-
AAHEFIEWLESA-OH (Compound 19)
H-H-Aib-HGTFTSDYSKYLEE-K(Hexadecanoyl-isoGlu)-
AAHEFVEWLESA-NH$_2$ (Compound 20)
H-H-Aib-QGTFTSDYSKYLEE-K(Hexadecanoyl-isoGlu)-
AAKDFIEWLESA-NH$_2$ (Compound 21)
H-H-Aib-QGTFTSDYSKYLES-K(Hexadecanoyl-isoGlu)-
AAEDFIEWLESA-NH$_2$ (Compound 22)
H-HSQGTFTSDYSKYLEE-K(Hexadecanoyl-isoGlu)-
AAKDFIEWLESA-NH$_2$ (Compound 23)
H-Aib-QGTFTSDYSKYLES-K(Hexadecanoyl-isoGlu)-
AAHDFVEWLESA-NH$_2$ (Compound 24)
H-H-Aib-QGTFTSDYSKYLES-K(Hexadecanoyl-isoGlu)-
AAEDFVEWLESA-NH$_2$ (Compound 25)
H-H-DSer-QGTFTSDYSKYLDE-K(Hexadecanoyl-isoGlu)-
AAKDFIEWLESA-NH$_2$

Example 2: General Synthesis of Acylated Glucagon Analogues

The peptide backbone was synthesized as described above for the general synthesis of glucagon analogues, with the exception that it was acylated on the side chain of a lysine residue with the peptide still attached to the resin and fully protected on the side chain groups, except the epsilon-amine on the lysine to be acylated. The lysine to be acylated was incorporated with the use of Fmoc-Lys(ivDde)-OH or Fmoc-Lys(Dde)-OH. The N-terminus of the peptide was protected with a Boc group using Boc$_2$O in NMP. While the peptide was still attached to the resin, the ivDde protecting group was selectively cleaved using 5% hydrazine hydrate in NMP. The unprotected lysine side chain was then first coupled with a spacer amino acid like Fmoc-Glu-OtBu, which was subsequently deprotected with piperidine and acylated with a fatty acid using standard peptide coupling methodology as described above. Alternatively, the histidine at the N-terminal may be incorporated from the beginning as Boc-His(Boc)-OH. Cleavage from the resin and purification were performed as described above.

Example 3: Glucagon Receptor and GLP-1-receptor Efficacy Assays

The cDNA encoding either the human glucagon receptor (Glucagon-R) (primary accession number P47871) or the human glucagon-like peptide 1 receptor (GLP-1R) (primary accession number P43220) were synthesized and cloned into a mammalian expression vector containing a Zeocin resistance marker.

The mammalian expression vectors encoding the Glucagon-R or the GLP-1-R were transfected into Chinese hamster ovary (CHO) cells by the Attractene method method. Stably expressing clones were obtained by Zeocin selection (250 µg/mL) upon limited dilution of cells resistant to the selection pressure. Glucagon-R and GLP-1-R cell clones expressing were picked, propagated and tested in the Glucagon-R and GLP-1-R efficacy assays as described below. One Glucagon-R expressing clone and one GLP-1-R expressing clone were chosen for compound profiling.

CHO cells expressing the human Glucagon-R, or human GLP-1-R were seeded 24 hours prior to the assay at 30,000 cells per well in 96-well microtiter plates in culture in 100 µl growth medium. On the day of analysis, growth medium was removed and the cells were washed once with 200 µl of assay buffer (Krebs-Ringer-buffer—KRBH). The buffer was removed and the cells were incubated for 15 min at room temperature in 10 µl KRBH (KRBH+10 mM HEPES, 5 mM NaHCO3, 0.1% (V/V) BSA) with 0.1 mM IBMX in deionized water containing increasing concentrations of test peptides. The reaction was stopped by the addition of lysis buffer (0.1% w/v BSA, 5 mM HEPES, 0.3% v/v Tween-20). After cell lysis for 10 min at room temperature, lysates were transferred to 384-well plates and 10 µl of acceptor/donor-bead mixture as contained in the AlphaScreen™ cAMP Functional Assay Kit was added. After one hour of incubation at room temperature in the dark, the cAMP content was determined applying the AlphaScreen™ cAMP Functional Assay Kit from Perkin-Elmer according to manufacturer instructions. EC$_{50}$ and relative efficacies compared to reference compounds (glucagon and GLP-1) were calculated applying computer aided curve fitting. The GLP-1/glucagon ratio is calculated as defined earlier. See Tables 1A and 1B.

TABLE 1A

| Compound | EC50 hGCGR CHO-K1 [nM] | EC50 hGLP-1R CHO-K1 [nM] | Ratio GLP-1/Glucagon |
| --- | --- | --- | --- |
| 1 | 0.90 | 0.54 | 0.60 |
| 2 | 0.31 | 0.77 | 2.48 |
| 3 | 0.35 | 0.91 | 2.60 |
| 4 | 1.56 | 0.38 | 0.24 |
| 5 | 0.46 | 0.16 | 0.35 |
| 6 | 0.46 | 0.35 | 0.76 |
| 7 | 0.45 | 0.27 | 0.60 |
| 8 | 0.29 | 0.41 | 1.41 |
| 9 | 0.25 | 0.35 | 1.40 |
| 10 | 0.23 | 0.23 | 1.00 |
| 11 | 0.61 | 0.64 | 1.05 |
| 12 | 0.43 | 0.37 | 0.86 |
| 13 | 0.98 | 0.51 | 0.52 |
| 14 | 0.54 | 0.53 | 0.98 |
| 15 | 0.61 | 0.19 | 0.31 |
| 16 | 1.58 | 0.20 | 0.13 |

TABLE 1B

| Compound | EC50 hGCGR CHO-K1 [nM] | EC50 hGLP-1R CHO-K1 [nM] | Ratio GLP-1/Glucagon |
|---|---|---|---|
| 17 | 0.05 nM | 0.23 nM | 4.6 |
| 18 | 0.14 nM | 0.87 nM | 6.2 |
| 19 | 0.08 nM | 0.27 nM | 3.38 |
| 20 | 0.68 nM | 0.23 nM | 0.34 |
| 21 | 1.32 nM | 0.12 nM | 0.09 |
| 22 | 0.10 nM | 0.24 nM | 2.40 |
| 23 | 0.25 nM | 0.13 nM | 0.52 |
| 24 | 0.92 nM | 0.11 nM | 0.12 |
| 25 | 0.16 nM | 0.31 nM | 1.94 |

The two sets of compounds were tested in experiments performed using the same protocol in different laboratories.

Example 4: Agonistic Activity on Endogenous GLP-1 Receptor

Agonistic activity of the test compounds on endogenous GLP-1 receptors was determined using a murine insulinoma cell line. Intracellular cAMP was used an indicator of receptor activation.

Cells were cultured for 24 h at a density of 10,000 cells/well in a 384-well plate. Medium was removed and 10 µL KRBH buffer (NaCl 130 mM, KCl 3.6 mM, $NaH_2PO_4$ 0.5 mM, $MgSO_4$ 0.5 mM, $CaCl_2$ 1.5 mM) containing test compound or GLP-1 (at increasing concentrations from 0.1 pM to 100 nM) or solvent control (0.1% (v/v) DMSO) was added to the wells for 15 minutes at a temperature of 26° C.

The cellular cAMP content is measured using the AlphaScreen cAMP Functional Assay Kit (Perkin Elmer). Measurement was performed using the Envision (PerkinElmer) according to manufacturer's recommendations.

All measurements were performed in quadruplicate.

Results were converted into cAMP concentrations using a cAMP standard curve prepared in KRBH buffer containing 0.1% (v/v) DMSO. The resulting cAMP curves were plotted as absolute cAMP concentrations (nM) over log (test compound concentration) and analyzed using the curve fitting program XLfit.

Parameters calculated to describe the both the potency as well as the agonistic activity of each test compound on the endogenous GLP-1 receptors were:

pEC50 (negative logarithmic value of EC50, a concentration resulting in a half-maximal elevation of cAMP levels, reflecting the potency of the test compound);
Percent control (% CTL) (% cAMP elevation for each test compound concentration normalized based on the GLP-1-induced maximum cAMP response (100% CTL)). See Table 2.

TABLE 2

| Compound | EC50 GLP-1R (murine insulinoma cells) [nM] |
|---|---|
| 1 | 1.47 |
| 2 | 1.41 |
| 3 | 1.06 |
| 4 | 0.95 |
| 5 | 0.54 |
| 6 | 1.14 |
| 7 | 0.84 |
| 8 | 0.95 |
| 9 | 1.02 |

TABLE 2-continued

| Compound | EC50 GLP-1R (murine insulinoma cells) [nM] |
|---|---|
| 10 | 0.33 |
| 11 | 1.01 |
| 12 | 1.62 |
| 13 | 1.06 |
| 14 | 0.72 |
| 15 | 0.30 |
| 16 | 0.33 |
| 17 | 0.89 |
| 18 | 0.99 |
| 19 | 0.33 |
| 20 | 0.27 |
| 21 | 0.30 |
| 22 | 0.35 |
| 23 | 0.31 |
| 24 | 0.33 |
| 25 | 0.41 |

Example 5: Agonistic Activity on Endogenous Glucagon Receptor

Agonistic activity of the test compounds on endogenous glucagon receptor was determined by measuring their effect on rate of glycogen synthesis in primary rat hepatocytes. Upon activation of the glucagon receptor, an inhibition of the glycogen synthesis rate is expected. Rate of glycogen synthesis was determined by counting the amount of radioactively labeled glucose incorporated into the cellular glycogen stores in a defined period of time.

Primary rat hepatocytes were cultured at a density of 40,000 cells/well in a 24-well plate for 24 hours at 37° C. and 5% $CO_2$.

Medium was discarded and the cells washed with PBS. 180 µl OF KRBH-based buffer containing 0.1% BSA and glucose at a concentration of 22.5 mM was then added to the wells, followed by test compound and 40 µCi/ml D-[U14C] glucose (20 µL each). Incubation was continued for 3 hours.

At the end of the incubation period, the incubation buffer was aspirated and cells washed once with ice-cold PBS before lysis by incubation for 30 min at room temperature with 100 µL 1 mol/l NaOH.

Cell lysates were transferred to 96-well filter plates and glycogen precipitated by incubating the filter-plates for 120 min at 4° C. followed by washing the filter plates 4 times with ice-cold ethanol (70%). The resulting precipitates were filtered to dryness and the amount of incorporated $^{14}$C-glucose determined by using a Topcount scintillation counter according to manufacturer's recommendations.

Wells with vehicle controls (0.1% (v/v) DMSO in KRBH buffer) were included as reference for non-inhibited glycogen synthesis (100% CTL). Wells without added D-[$U^{14}C$] glucose were included as controls for non-specific background signal (subtracted from all values). Endogenous glucagon peptide was used as a positive control.

All treatments were performed at least in triplicates.

Parameters calculated to describe the both the potency as well as the agonistic activity of each test compound on the endogenous glucagon receptor are pEC50 and % CTL.

% CTL is determined by calculating the percentage of CPM/well in the presence of the test compound compared to the CPM/well of the vehicle control after subtracting the background CPM/well:

[CPM/well(basal)−CPM/well(sample)]*100/[CPM/well(basal)−CPM/well(control)]

An activator of the glucagon receptor will result in an inhibition of the glycogen synthesis rate and will give % CTL values between 0% CTL (complete inhibition) and 100% CTL (no observable inhibition).

The resulting activity curves were plotted as absolute counts (unit: cpm/sample) over log (test compound concentration) and analyzed using the curve fitting program XLfit.

pEC50 (negative logarithmic value of EC50) reflects the potency of the test compound.

TABLE 3

| Compound | EC50 GLP-1R Rat hepat. [nM] |
|---|---|
| 1 | 0.13 |
| 1 | 0.02 |
| 2 | 0.43 |
| 3 | 0.16 |
| 4 | 0.35 |
| 5 | 0.03 |
| 6 | 2.87 |
| 7 | 1.92 |
| 8 | 1.10 |
| 9 | 0.37 |
| 10 | 0.04 |
| 12 | 0.24 |
| 13 | 0.67 |
| 14 | 0.10 |
| 15 | 0.17 |
| 16 | 1.85 |
| 17 | 0.18 |
| 18 | 0.18 |
| 19 | 0.06 |
| 20 | 0.39 |
| 21 | 3.40 |
| 22 | 0.28 |
| 23 | 1.32 |
| 24 | 6.15 |
| 25 | 0.15 |

The terms $EC_{50}$ and $pEC_{50}$ quoted in relation to GLP-1R activation could equally be regarded as $IC_{50}$ and $pIC_{50}$ in relation to glycogen synthesis.

Example 6: Estimate of Pharmacokinetic Parameters

Pharmacokinetic parameters of the test compounds were determined after subcutaneous and intravenous administration to C57Bl/6J mice.

8 week old male C57Bl/6J mice were obtained from Taconic (Denmark) weighing approximately 20-25 g at time of arrival at the test facility. The mice were caged in European standard cages type III with light cycle of 12-hour dark and 12-hour light (lights on 06.00). Both diet, Altromin 1324 (Altromin, Germany), and water was administered ad libitum during the whole experimental period. The 8-11 week animals were imported to the laboratory at least 7 days before the start up of the experimental procedure in order to assure proper acclimatization. After sampling the mice were euthanized by cervical dislocation.

The compounds were first dissolved in 0.096% aqueous ammonia to a nominal concentration of 2 mg/ml, and then diluted to the desired dosing strength (4 µM) in sterile PBS containing 25 mM phosphate buffer, pH 7.4. Subcutaneous and intravenous injections corresponding to 20 nmol/kg were given. The GLP-1-glucagon dual agonists were administered for subcutaneous dosing in the neck region and via a lateral tail vein for intravenous dosing.

Blood samples (250 µl) were collected from the periorbital plexus at time points 0.5, 2, 4, 6, 12, 16, 20, 24 h for subcutaneous and 10, 30 min, 3, 6, 12, 18, 24 h for intravenous administration into ice-chilled $K_3$EDTA tubes and centrifuged for 5 minutes at 4° C. within 20 minutes of sampling. Plasma (>100 µl) was separated to ice-chilled Micronic tubes, immediately frozen, and kept at −70° C. until analysed for plasma concentration for the respective GLP-1-glucagon compound using LC-MS/MS. Individual plasma concentration-time profiles were analysed by a non-compartmental approach in WinNonLin v6.3 (Pharsight inc, Mountain View, Calif., USA), and the resulting pharmacokinetic parameters determined. See Table 4.

TABLE 4

| | SC | | | | IV | |
|---|---|---|---|---|---|---|
| Compound | Mean Residence Time (hr) | Bioavailability (%) | Tmax (hr) | Terminal half life (hr) | Clearance (L/hr/kg) | Terminal half life (hr) |
| 1 | 12.6 | 52 | 4 | 6.2 | 0.0102 | 5.2 |
| 2 | 11.2 | 59 | 4 | 5.1 | 0.0111 | 5.0 |
| 3 | 9.8 | 52 | 6 | 3.9 | 0.0115 | 4.1 |
| 4 | 12.5 | 53 | 4 | 6.4 | 0.0111 | 7.4 |
| 5 | 7.6 | 81 | 4 | 3.8 | 0.0111 | 4.0 |
| 6 | 10.6 | 47 | 4 | 4.3 | 0.0094 | 3.7 |
| 7 | 12.8 | 75 | 4 | 8.6 | 0.0132 | 5.5 |
| 8 | 8.1 | 42 | 4 | 4.1 | 0.0077 | 3.9 |
| 9 | 4.7 | 34 | 2 | 2.9 | 0.0383 | 0.9 |
| 10 | 6.5 | 80 | 2 | 3.7 | 0.0213 | 3.0 |
| 11 | 12.5 | 64 | 4 | 5.0 | 0.0094 | 3.9 |
| 12 | 8.3 | 43 | 6 | 4.3 | 0.0135 | 4.1 |
| 13 | 14.7 | 76 | 4 | 8.6 | 0.0089 | 6.3 |
| 14 | 12.2 | 64 | 4 | 6.1 | 0.0135 | 6.2 |
| 15 | 17.4 | 97 | 6 | 10.5 | 0.0077 | 6.0 |
| 16 | 7.5 | 80 | 2 | 5.0 | 0.0187 | 4.8 |

Example 7: Oral Glucose Tolerance Test (OGTT) in C57BL/6J Mice

Male C57BL/6J mice were fasted for 10 h before they received an oral glucose bolus of 2 g/kg body weight. Peptides were dissolved in saline buffered with 25 mM phosphate and administered at a dose of 10 nmol/kg body weight by subcutaneous injection 4 h before the glucose bolus. Control animals received a vehicle injection only. Group size was 7 animals per group. A pre-dose and a pre-glucose (0 min) blood sample were obtained by tail bleeding and blood glucose was measured with a glucometer. Additional samples of tail blood for measuring blood glucose were obtained 15 min, 30 min, 60 min, 90 min and 120 min after the glucose challenge. Glucose excursion was quantified by calculating the total area under the blood glucose-time curve (AUC) between 0 min and 120 min. Calculation of AUC was done by the trapezoidal rule without baseline correction. The data are presented as mean±S.E.M. Statistical comparisons were conducted by one-way ANOVA followed by Tukey's post test. Vehicle alone was used as a control. See Table 5.

TABLE 5

| Compound | AUC (% Ctrl) |
| --- | --- |
| 1 | 66 |
| 2 | 66 |
| 3 | 70 |
| 4 | 65 |
| 5 | 46 |
| 6 | 50 |
| 7 | 57 |
| 8 | 50 |
| 9 | 57 |
| 10 | 46 |
| 11 | 61 |
| 12 | 56 |
| 13 | 55 |
| 14 | 59 |
| 15 | 42 |
| 16 | 44 |

Example 8: Sub-chronic Effects of Glucagon-GLP-1 Receptor Dual Acting Agonists on Adiposity in Diet-induced Obese C57BL/6J Mice Male C57BL/6J mice (Taconic A/S, Denmark) at an age of 5 weeks were maintained on a 12:12 hour light-dark cycle on a high-fat diet (60% of total energy from fat, D12492, Research Diet Inc.) for 20 weeks. All mice (housed 2 per cage) were then mock-treated for a week to acclimatize the animals to handling and injections. Subsequently, the mice were stratified according to body fat mass (measured by magnetic resonance technique) and body weight into 9 groups (n=9-12). Animals were thereafter treated twice daily with subcutaneous injections (5 ml/kg) of vehicle (25 mM phosphate buffer, pH 7.4) or test substances (5 nmol/kg per administration, in equivalent amount of vehicle) for a total of 31 days. The daily injections were given at the start and at the end of the light phase. Body weight, food and water intake were determined daily throughout the study. The data are presented in Table 6 as mean body weight change ±S.E.M. S.E.M. is defined as standard error of the mean and was calculated using the formula: S.E.M.=SD/square root (n), where SD is the standard deviation and n the number of observations (in this case animals/group).

Statistical analyses were performed using Graph Pad Prism version 5. The measured parameters were compared using one-way ANOVA followed by Dunnett's multiple comparison test. Differences were considered statistically significant at p<0.05.

TABLE 6

| Treatment Group | Mean body weight change (%) | SEM | Significance of difference vs. vehicle group |
| --- | --- | --- | --- |
| Vehicle | 4.8 | 1.3 | |
| Liraglutide | -2.3 | 1.5 | ** |
| Compound 2 | -5.1 | 1.9 | *** |
| Compound 7 | -8.7 | 1.5 | *** |
| Compound 14 | -9.5 | 1.1 | *** |
| Compound 15 | -10.9 | 1.6 | *** |
| Compound 16 | -12.2 | 1.1 | *** |

- p < 0.01, * - p < 0.001 vs vehicle

---

The invention claimed is:

1. A compound having the formula:

R¹—X—Z—R² wherein
R¹ is H, C₁₋₄ alkyl, acetyl, formyl, benzoyl or trifluoroacetyl;
R² is OH or NH₂;
X is a peptide which has the formula:

(SEQ ID NO: 4)
H-Aib-QGTFTSDYSKYLDEKAAKDFIEWLLSA, (SEQ ID NO: 5)
H-Aib-QGTFTSDYSKYLDSKAAHDFVEWLESA, (SEQ ID NO: 6)
HSQGTFTSDYSRYLDSKAAEDFVEWLLRA, (SEQ ID NO: 7)
HSQGTFTSDYSKYLDSKAAEDFVEWLLRA, (SEQ ID NO: 8)
HSQGTFTSDYSKYLDSKAAHDFVEWLLS, (SEQ ID NO: 9)
HSQGTFTSDYSKYLDSKAAHDFVEWLLR, (SEQ ID NO: 10)
HSQGTFTSDYSKYLDEKAAHEFVEWLESA, (SEQ ID NO: 11)
H-Aib-QGTFTSDYSKYLDEKRAKDFIEWLLS,
or (SEQ ID NO: 12)
HSQGTFTSDYSRYLDSKAAHDFVEWLLSA, (SEQ ID NO: 17)
H-Aib-HGTFTSDYSKYLESKAAEEFIEWLESA, (SEQ ID NO: 18)
HSHGTFTSDYSKYLEEKAAHEFIEWLESA, (SEQ ID NO: 19)
H-Aib-HGTFTSDYSKYLEEKAAHEFVEWLESA, and Z is absent or is a sequence of 1-20 amino acid units independently selected from the group consisting of Ala, Leu, Ser, Thr, Tyr, Cys, Glu, Lys, Arg, Dbu, Dpr and Orn;
or a pharmaceutically acceptable salt thereof.

2. A compound according to claim 1, wherein one or more of the amino acid side chains in the peptide X or Z is conjugated to a lipophilic substituent.

3. A compound according to claim 2 wherein peptide X has the formula:

(SEQ ID NO: 4)
H-Aib-QGTFTSDYSKYLDE-K(Hexadecanoyl-isoGlu)-AAKDFIEWLLSA, (SEQ ID NO: 5)
H-Aib-QGTFTSDYSKYLDS-K(Hexadecanoyl-isoGlu)-AAHDFVEWLESA, (SEQ ID NO: 6)
HSQGTFTSDYSRYLDS-K(Hexadecanoyl-isoGlu)-AAEDFVEWLLRA, (SEQ ID NO: 7)
HSQGTFTSDYSKYLDS-K(Hexadecanoyl-isoGlu)-AAEDFVEWLLRA, (SEQ ID NO: 8)
HSQGTFTSDYSKYLDS-K(Hexadecanoyl-isoGlu)-AAHDFVEWLLS, (SEQ ID NO: 9)
HSQGTFTSDYSKYLDS-K(Hexadecanoyl-isoGlu)-AAHDFVEWLLR, (SEQ ID NO: 10)
HSQGTFTSDYSKYLDE-K(Hexadecanoyl-isoGlu)-AAHEFVEWLESA, (SEQ ID NO: 11)
H-Aib-QGTFTSDYSKYLDE-K(Hexadecanoyl-isoGlu)-RAKDFIEWLLS, (SEQ ID NO: 12)
HSQGTFTSDYSRYLDS-K(Hexadecanoyl-isoGlu)-AAHDFVEWLLSA, (SEQ ID NO: 17)
H-Aib-HGTFTSDYSKYLES-K(Hexadecanoyl-isoGlu)-AAEEFIEWLESA, (SEQ ID NO: 18)
HSHGTFTSDSKYLEE-K(Hexadecanoyl-isoGlu)-AAHEFIEWLESA, (SEQ ID NO: 19)
H-Aib-HGTFTSDYSKYLEE-K(Hexadecanoyl-isoGlu)-AAHEFVEWLESA, or a pharmaceutically acceptable salt thereof.

4. A compound according to claim 3 having the formula:

(Compound 4)
(SEQ ID NO: 4)
H-H-Aib-QGTFTSDYSKYLDE-K(Hexadecanoyl-isoGlu)-AAKDFIEWLLSA-NH₂, (Compound 5)
(SEQ ID NO: 5)
H-H-Aib-QGTFTSDYSKYLDS-K(Hexadecanoyl-isoGlu)-AAHDFVEWLESA-NH₂, (Compound 6)
(SEQ ID NO: 6)
H-HSQGTFTSDYSRYLDS-K(Hexadecanoyl-isoGlu)-AAEDFVEWLLRA-NH₂, (Compound 7)
(SEQ ID NO: 7)
H-HSQGTFTSDYSKYLDS-K(Hexadecanoyl-isoGlu)-AAEDFVEWLLRA-NH₂, (Compound 8)
(SEQ ID NO: 8)
H-HSQGTFTSDYSKYLDS-K(Hexadecanoyl-isoGlu)-AAHDFVEWLLS-NH₂, -continued (Compound 9)
(SEQ ID NO: 9)
H-HSQGTFTSDYSKYLDS-K(Hexadecanoyl-isoGlu)-
AAHDFVEWLLR-OH, (Compound 10)
(SEQ ID NO: 10)
H-HSQGTFTSDYSKYLDE-K(Hexadecanoyl-isoGlu)-
AAHEFVEWLESA-NH$_2$, (Compound 11)
(SEQ ID NO: 11)
H-H-Aib-QGTFTSDYSKYLDE-K(Hexadecanoyl-isoGlu)-
RAKDFIEWLLS-OH, (Compound 12)
(SEQ ID NO: 12)
H-HSQGTFTSDYSRYLDS-K(Hexadecanoyl-isoGlu)-
AAHDFVEWLLSA-NH$_2$, (Compound 17)
(SEQ ID NO: 17)
H-H-Aib-HGTFTSDYSKYLES-K(Hexadecanoyl-isoGlu)-
AAEEFIEWLESA-OH, (Compound 18)
(SEQ ID NO: 18)
H-HSHGTFTSDYSKYLEE-K(Hexadecanoyl-isoGlu)-
AAHEFIEWLESA-OH, (Compound 19)
(SEQ ID NO: 19)
H-H-Aib-HGTFTSDYSKYLEE-K(Hexadecanoyl-isoGlu)-
AAHEFVEWLESA-NH$_2$, or a pharmaceutically acceptable salt thereof.

\* \* \* \* \*